US011302426B1

United States Patent
Winlo et al.

(10) Patent No.: US 11,302,426 B1
(45) Date of Patent: Apr. 12, 2022

(54) UNIFIED DATA INTERFACE AND SYSTEM

(71) Applicant: Palantir Technologies Inc., Palo Alto, CA (US)

(72) Inventors: Michael Winlo, Palo Alto, CA (US); Chris Burchhardt, Palo Alto, CA (US); Kyle McLain, Palo Alto, CA (US); Harsh Pandey, Menlo Park, CA (US); Tayler Cox, Los Altos Hills, CA (US); Lekan Wang, Palo Alto, CA (US)

(73) Assignee: Palantir Technologies Inc., Denver, CO (US)

( * ) Notice: Subject to any disclaimer, the term of this patent is extended or adjusted under 35 U.S.C. 154(b) by 0 days.

(21) Appl. No.: 14/975,215

(22) Filed: Dec. 18, 2015

Related U.S. Application Data

(60) Provisional application No. 62/099,321, filed on Jan. 2, 2015.

(51) Int. Cl.
*G16H 10/60* (2018.01)
*G16H 40/20* (2018.01)

(52) U.S. Cl.
CPC ............ *G16H 10/60* (2018.01); *G16H 40/20* (2018.01)

(58) Field of Classification Search
CPC ..... G06F 19/322; G06F 19/327; G16H 10/60; G16H 40/20; G16H 15/00; G16H 50/30
See application file for complete search history.

(56) References Cited

U.S. PATENT DOCUMENTS

| | | | |
|---|---|---|---|
| 5,241,625 | A | 8/1993 | Epard et al. |
| 5,670,987 | A | 9/1997 | Doi et al. |
| 5,819,226 | A | 10/1998 | Gopinathan et al. |
| 5,826,021 | A | 10/1998 | Masters et al. |
| 5,832,218 | A | 11/1998 | Gibbs et al. |

(Continued)

FOREIGN PATENT DOCUMENTS

| | | |
|---|---|---|
| CN | 102546446 | 7/2012 |
| CN | 103167093 | 6/2013 |

(Continued)

OTHER PUBLICATIONS

Jul. 2015 Update Appendix 1: Examples published by the USPTO.*
(Continued)

*Primary Examiner* — Eliza A Lam
(74) *Attorney, Agent, or Firm* — Knobbe Martens Olson & Bear LLP

(57) ABSTRACT

Various systems and methods are provided that aggregate, analyze, and display health data for users. The system aggregates data stored in various databases. For example, the system retrieves data from these databases, maps the data to a set of common terms based on an ontology, and displays such information to an entity accessing the system. Rather than converting the data stored in the databases into a standardized format, the system includes a set of ontologies that provide a correlation between a first set of fields and a second set of fields. The system determines a correlation between a first field in the first set of fields and a second field in the second set of fields using the ontology, stores data retrieved from the database in a second database in association with the second field, and displays the data associated with the first field under the second field.

20 Claims, 16 Drawing Sheets

(56) References Cited

U.S. PATENT DOCUMENTS

| | | |
|---|---|---|
| 5,845,300 A | 12/1998 | Comer |
| 5,878,434 A | 3/1999 | Draper et al. |
| 5,892,900 A | 4/1999 | Ginter et al. |
| 5,893,072 A | 4/1999 | Zizzamia |
| 5,897,636 A | 4/1999 | Kaeser |
| 5,966,706 A | 10/1999 | Biliris et al. |
| 5,999,911 A | 12/1999 | Berg et al. |
| 6,006,242 A | 12/1999 | Poole et al. |
| 6,057,757 A | 5/2000 | Arrowsmith et al. |
| 6,065,026 A | 5/2000 | Cornelia et al. |
| 6,094,643 A | 7/2000 | Anderson et al. |
| 6,134,582 A | 10/2000 | Kennedy |
| 6,161,098 A | 12/2000 | Wallman |
| 6,219,053 B1 | 4/2001 | Tachibana et al. |
| 6,232,971 B1 | 5/2001 | Haynes |
| 6,237,138 B1 | 5/2001 | Hameluck et al. |
| 6,243,706 B1 | 6/2001 | Moreau et al. |
| 6,243,717 B1 | 6/2001 | Gordon et al. |
| 6,279,018 B1 | 8/2001 | Kudrolli et al. |
| 6,341,310 B1 | 1/2002 | Leshem et al. |
| 6,369,835 B1 | 4/2002 | Lin |
| 6,370,538 B1 | 4/2002 | Lamping et al. |
| 6,430,305 B1 | 8/2002 | Decker |
| 6,463,404 B1 | 10/2002 | Appleby |
| 6,505,196 B2 | 1/2003 | Drucker et al. |
| 6,519,627 B1 | 2/2003 | Dan et al. |
| 6,523,019 B1 | 2/2003 | Borthwick |
| 6,549,944 B1 | 4/2003 | Weinberg et al. |
| 6,714,936 B1 | 3/2004 | Nevin, III |
| 6,820,135 B1 | 11/2004 | Dingman |
| 6,839,745 B1 | 1/2005 | Dingari et al. |
| 6,944,821 B1 | 9/2005 | Bates et al. |
| 6,978,419 B1 | 12/2005 | Kantrowitz |
| 6,980,984 B1 | 12/2005 | Huffman et al. |
| 7,058,648 B1 | 6/2006 | Lightfoot et al. |
| 7,086,028 B1 | 8/2006 | Davis et al. |
| 7,089,541 B2 | 8/2006 | Ungar |
| 7,139,800 B2 | 11/2006 | Bellotti et al. |
| 7,168,039 B2 | 1/2007 | Bertram |
| 7,171,427 B2 | 1/2007 | Witowski et al. |
| 7,174,377 B2 | 2/2007 | Bernard et al. |
| 7,213,030 B1 | 5/2007 | Jenkins |
| 7,278,105 B1 | 10/2007 | Kitts |
| 7,379,903 B2 | 5/2008 | Caballero et al. |
| 7,383,239 B2 | 6/2008 | Bonissone |
| 7,392,254 B1 | 6/2008 | Jenkins |
| 7,403,942 B1 | 7/2008 | Bayliss |
| 7,418,431 B1 | 8/2008 | Nies et al. |
| 7,426,654 B2 | 9/2008 | Adams et al. |
| 7,441,182 B2 | 10/2008 | Beilinson et al. |
| 7,454,466 B2 | 11/2008 | Bellotti et al. |
| 7,461,158 B2 | 12/2008 | Rider et al. |
| 7,467,375 B2 | 12/2008 | Tondreau et al. |
| 7,525,422 B2 | 4/2009 | Bishop et al. |
| 7,617,232 B2 | 11/2009 | Gabbert et al. |
| 7,627,489 B2 | 12/2009 | Schaeffer et al. |
| 7,627,812 B2 | 12/2009 | Chamberlain et al. |
| 7,634,717 B2 | 12/2009 | Chamberlain et al. |
| 7,703,021 B1 | 4/2010 | Flam |
| 7,716,077 B1 | 5/2010 | Mikurak |
| 7,725,547 B2 | 5/2010 | Albertson et al. |
| 7,756,843 B1 | 7/2010 | Palmer |
| 7,757,220 B2 | 7/2010 | Griffith et al. |
| 7,765,489 B1 | 7/2010 | Shah et al. |
| 7,770,100 B2 | 8/2010 | Chamberlain et al. |
| 7,813,937 B1 | 10/2010 | Pathria et al. |
| 7,818,658 B2 | 10/2010 | Chen |
| 7,827,045 B2 | 11/2010 | Madill et al. |
| 7,877,421 B2 | 1/2011 | Berger et al. |
| 7,880,921 B2 | 2/2011 | Dattilo et al. |
| 7,899,796 B1 | 3/2011 | Borthwick et al. |
| 7,912,842 B1 | 3/2011 | Bayliss |
| 7,917,376 B2 | 3/2011 | Bellin et al. |
| 7,941,321 B2 | 5/2011 | Greenstein et al. |
| 7,941,336 B1 | 5/2011 | Robin-Jan |
| 7,966,199 B1 | 5/2011 | Frasher |
| 7,958,147 B1 | 6/2011 | Turner et al. |
| 7,962,495 B2 | 6/2011 | Jain et al. |
| 7,962,848 B2 | 6/2011 | Bertram |
| 8,001,465 B2 | 8/2011 | Kudrolli et al. |
| 8,001,482 B2 | 8/2011 | Bhattiprolu et al. |
| 8,010,507 B2 | 8/2011 | Poston et al. |
| 8,015,487 B2 | 9/2011 | Roy et al. |
| 8,036,971 B2 | 10/2011 | Aymeloglu et al. |
| 8,046,283 B2 | 10/2011 | Burns |
| 8,054,756 B2 | 11/2011 | Chand et al. |
| 8,073,857 B2 | 12/2011 | Sreekanth |
| 8,117,022 B2 | 2/2012 | Linker |
| 8,126,848 B2 | 2/2012 | Wagner |
| 8,147,715 B2 | 4/2012 | Bruckhaus et al. |
| 8,214,232 B2 | 7/2012 | Tyler et al. |
| 8,214,490 B1 | 7/2012 | Vos et al. |
| 8,225,201 B2 | 7/2012 | Michael |
| 8,229,902 B2 | 7/2012 | Vishniac et al. |
| 8,230,333 B2 | 7/2012 | Decherd et al. |
| 8,290,838 B1 | 10/2012 | Thakur et al. |
| 8,301,464 B1 | 10/2012 | Cave et al. |
| 8,302,855 B2 | 11/2012 | Ma et al. |
| 8,364,642 B1 | 1/2013 | Garrod |
| 8,417,715 B1 | 4/2013 | Bruckhaus et al. |
| 8,429,527 B1 | 4/2013 | Arbogast |
| 8,447,722 B1 | 5/2013 | Ahuja et al. |
| 8,473,454 B2 | 6/2013 | Evanitsky et al. |
| 8,484,115 B2 | 7/2013 | Aymeloglu et al. |
| 8,489,623 B2 | 7/2013 | Jain et al. |
| 8,489,641 B1 | 7/2013 | Seefeld et al. |
| 8,514,082 B2 | 8/2013 | Cova et al. |
| 8,515,912 B2 | 8/2013 | Garrod et al. |
| 8,527,461 B2 | 9/2013 | Ducott, III et al. |
| 8,538,827 B1 * | 9/2013 | Dryer ................ G06Q 30/00 705/26.1 |
| 8,554,579 B2 | 10/2013 | Tribble et al. |
| 8,554,719 B2 | 10/2013 | McGrew |
| 8,577,911 B1 | 11/2013 | Stepinski et al. |
| 8,578,500 B2 | 11/2013 | Long |
| 8,589,273 B2 | 11/2013 | Creeden et al. |
| 8,600,872 B1 | 12/2013 | Yan |
| 8,601,326 B1 | 12/2013 | Kim |
| 8,620,641 B2 | 12/2013 | Farnsworth et al. |
| 8,639,522 B2 | 1/2014 | Pathria et al. |
| 8,639,552 B1 | 1/2014 | Chen et al. |
| 8,655,687 B2 | 2/2014 | Zizzamia |
| 8,666,861 B2 | 3/2014 | Li et al. |
| 8,682,696 B1 | 3/2014 | Shanmugam |
| 8,688,573 B1 | 4/2014 | Rukonic et al. |
| 8,689,108 B1 | 4/2014 | Duffield et al. |
| 8,713,467 B1 | 4/2014 | Goldenberg et al. |
| 8,732,574 B2 | 5/2014 | Burr et al. |
| 8,744,890 B1 | 6/2014 | Bernier |
| 8,798,354 B1 | 8/2014 | Bunzel et al. |
| 8,799,313 B2 | 8/2014 | Satlow |
| 8,812,960 B1 | 8/2014 | Sun et al. |
| 8,903,717 B2 | 12/2014 | Elliot |
| 8,924,388 B2 | 12/2014 | Elliot et al. |
| 8,924,389 B2 | 12/2014 | Elliot et al. |
| 8,938,686 B1 | 1/2015 | Erenrich et al. |
| 8,949,164 B1 | 2/2015 | Mohler |
| 8,972,336 B2 * | 3/2015 | Jagota ................ G06Q 30/02 707/602 |
| 8,984,390 B2 | 3/2015 | Aymeloglu et al. |
| 9,032,531 B1 | 5/2015 | Scorvo et al. |
| 9,058,315 B2 | 6/2015 | Burr et al. |
| 9,100,428 B1 | 8/2015 | Visbal |
| 9,105,000 B1 | 8/2015 | White et al. |
| 9,129,219 B1 | 9/2015 | Robertson et al. |
| 9,208,285 B1 * | 12/2015 | Campbell .............. G06Q 50/24 |
| 9,418,337 B1 | 8/2016 | Elser et al. |
| 9,836,580 B2 | 12/2017 | Fendell et al. |
| 2001/0021936 A1 | 9/2001 | Bertram |
| 2001/0027424 A1 | 10/2001 | Torigoe |
| 2002/0032677 A1 | 3/2002 | Moregenthaler et al. |
| 2002/0035590 A1 | 3/2002 | Eibach et al. |
| 2002/0065708 A1 | 5/2002 | Senay et al. |
| 2002/0095360 A1 | 7/2002 | Joao |

(56) References Cited

U.S. PATENT DOCUMENTS

| | | |
|---|---|---|
| 2002/0095658 A1 | 7/2002 | Shulman |
| 2002/0103705 A1 | 8/2002 | Brady |
| 2002/0130907 A1 | 9/2002 | Chi et al. |
| 2002/0147805 A1 | 10/2002 | Leshem et al. |
| 2002/0174201 A1 | 11/2002 | Ramer et al. |
| 2002/0194119 A1 | 12/2002 | Wright et al. |
| 2003/0033347 A1 | 2/2003 | Bolle et al. |
| 2003/0036927 A1 | 2/2003 | Bowen |
| 2003/0093401 A1 | 5/2003 | Czahowski et al. |
| 2003/0093755 A1 | 5/2003 | O'Carroll |
| 2003/0105759 A1 | 6/2003 | Bess et al. |
| 2003/0115481 A1 | 6/2003 | Baird et al. |
| 2003/0126102 A1 | 7/2003 | Borthwick |
| 2003/0163352 A1 | 8/2003 | Surpin et al. |
| 2003/0177112 A1 | 9/2003 | Gardner |
| 2003/0182313 A1 | 9/2003 | Federwisch et al. |
| 2003/0200217 A1 | 10/2003 | Ackerman |
| 2003/0212718 A1 | 11/2003 | Tester |
| 2004/0003009 A1 | 1/2004 | Wilmot |
| 2004/0006523 A1 | 1/2004 | Coker |
| 2004/0034570 A1 | 2/2004 | Davis |
| 2004/0044648 A1 | 3/2004 | Anfindsen et al. |
| 2004/0083466 A1 | 4/2004 | Dapp et al. |
| 2004/0085318 A1 | 5/2004 | Hassler et al. |
| 2004/0088177 A1 | 5/2004 | Travis et al. |
| 2004/0095349 A1 | 5/2004 | Bito et al. |
| 2004/0111480 A1 | 6/2004 | Yue |
| 2004/0117387 A1 | 6/2004 | Civetta et al. |
| 2004/0126840 A1 | 7/2004 | Cheng et al. |
| 2004/0153418 A1 | 8/2004 | Hanweck |
| 2004/0153451 A1 | 8/2004 | Philips et al. |
| 2004/0181554 A1 | 9/2004 | Heckerman et al. |
| 2004/0205492 A1 | 10/2004 | Newsome |
| 2004/0210763 A1 | 10/2004 | Jonas |
| 2004/0236688 A1 | 11/2004 | Bozeman |
| 2005/0010472 A1 | 1/2005 | Quatse et al. |
| 2005/0028094 A1 | 2/2005 | Allyn |
| 2005/0039116 A1 | 2/2005 | Slack-Smith |
| 2005/0086207 A1 | 4/2005 | Heuer et al. |
| 2005/0091186 A1 | 4/2005 | Alon |
| 2005/0097441 A1 | 5/2005 | Herbach et al. |
| 2005/0108063 A1 | 5/2005 | Madill et al. |
| 2005/0125715 A1 | 6/2005 | Di Franco et al. |
| 2005/0131935 A1 | 6/2005 | O'Leary et al. |
| 2005/0133588 A1 | 6/2005 | Williams |
| 2005/0149455 A1 | 7/2005 | Bruesewitz et al. |
| 2005/0149527 A1 | 7/2005 | Berlin |
| 2005/0154628 A1 | 7/2005 | Eckart et al. |
| 2005/0154769 A1 | 7/2005 | Eckart et al. |
| 2005/0180330 A1 | 8/2005 | Shapiro |
| 2005/0182654 A1 | 8/2005 | Abolfathi et al. |
| 2005/0262512 A1 | 11/2005 | Schmidt et al. |
| 2006/0010130 A1 | 1/2006 | Leff et al. |
| 2006/0026120 A1 | 2/2006 | Carolan et al. |
| 2006/0026170 A1 | 2/2006 | Kreitler et al. |
| 2006/0026561 A1 | 2/2006 | Bauman et al. |
| 2006/0031779 A1 | 2/2006 | Theurer et al. |
| 2006/0045470 A1 | 3/2006 | Poslinski et al. |
| 2006/0053097 A1 | 3/2006 | King et al. |
| 2006/0053170 A1 | 3/2006 | Hill et al. |
| 2006/0059423 A1 | 3/2006 | Lehmann et al. |
| 2006/0074866 A1 | 4/2006 | Chamberlain et al. |
| 2006/0080139 A1 | 4/2006 | Mainzer |
| 2006/0080316 A1 | 4/2006 | Gilmore et al. |
| 2006/0080619 A1 | 4/2006 | Carlson et al. |
| 2006/0129746 A1 | 6/2006 | Porter |
| 2006/0136513 A1 | 6/2006 | Ngo et al. |
| 2006/0142949 A1 | 6/2006 | Helt |
| 2006/0143034 A1 | 6/2006 | Rothermel |
| 2006/0143075 A1 | 6/2006 | Carr et al. |
| 2006/0143079 A1 | 6/2006 | Basak et al. |
| 2006/0149596 A1 | 7/2006 | Surpin et al. |
| 2006/0178915 A1 | 8/2006 | Chao |
| 2006/0218206 A1 | 9/2006 | Bourbonnais et al. |
| 2006/0218941 A1 | 9/2006 | Grossman et al. |
| 2006/0241974 A1 | 10/2006 | Chao et al. |
| 2006/0253502 A1 | 11/2006 | Raman et al. |
| 2006/0265417 A1 | 11/2006 | Amato et al. |
| 2006/0277460 A1 | 12/2006 | Forstall et al. |
| 2007/0000999 A1 | 1/2007 | Kubo et al. |
| 2007/0011304 A1 | 1/2007 | Error |
| 2007/0038646 A1 | 2/2007 | Thota |
| 2007/0043686 A1 | 2/2007 | Teng et al. |
| 2007/0061259 A1 | 3/2007 | Zoldi et al. |
| 2007/0061752 A1 | 3/2007 | Cory |
| 2007/0067285 A1 | 3/2007 | Blume |
| 2007/0106582 A1 | 5/2007 | Baker et al. |
| 2007/0113164 A1 | 5/2007 | Hansen et al. |
| 2007/0136095 A1 | 6/2007 | Weinstein |
| 2007/0150801 A1 | 6/2007 | Chidlovskii et al. |
| 2007/0156673 A1 | 7/2007 | Maga |
| 2007/0168871 A1 | 7/2007 | Jenkins |
| 2007/0178501 A1 | 8/2007 | Rabinowitz et al. |
| 2007/0185867 A1 | 8/2007 | Maga |
| 2007/0192143 A1 | 8/2007 | Krishnan et al. |
| 2007/0233756 A1 | 10/2007 | D'Souza et al. |
| 2007/0239606 A1 | 10/2007 | Eisen |
| 2007/0245339 A1 | 10/2007 | Bauman et al. |
| 2007/0266336 A1 | 11/2007 | Nojima et al. |
| 2007/0271317 A1 | 11/2007 | Carmel |
| 2007/0284433 A1 | 12/2007 | Domenica et al. |
| 2007/0295797 A1 | 12/2007 | Herman et al. |
| 2007/0299697 A1 | 12/2007 | Friedlander et al. |
| 2008/0005063 A1 | 1/2008 | Seeds |
| 2008/0016155 A1 | 1/2008 | Khalatian |
| 2008/0046481 A1 | 2/2008 | Gould et al. |
| 2008/0069081 A1 | 3/2008 | Chand et al. |
| 2008/0077597 A1 | 3/2008 | Butler |
| 2008/0077642 A1 | 3/2008 | Carbone et al. |
| 2008/0091693 A1 | 4/2008 | Murthy |
| 2008/0103798 A1 | 5/2008 | Domenikos et al. |
| 2008/0103996 A1 | 5/2008 | Forman et al. |
| 2008/0109714 A1 | 5/2008 | Kumar et al. |
| 2008/0126344 A1 | 5/2008 | Hoffman et al. |
| 2008/0126951 A1 | 5/2008 | Sood et al. |
| 2008/0140387 A1 | 6/2008 | Linker |
| 2008/0140576 A1 | 6/2008 | Lewis et al. |
| 2008/0155440 A1 | 6/2008 | Trevor et al. |
| 2008/0172257 A1 | 7/2008 | Bisker et al. |
| 2008/0172607 A1 | 7/2008 | Baer |
| 2008/0195417 A1 | 8/2008 | Surpin et al. |
| 2008/0195421 A1 | 8/2008 | Ludwig et al. |
| 2008/0195672 A1 | 8/2008 | Hamel et al. |
| 2008/0208855 A1* | 8/2008 | Lingenfelder ........ G06F 16/258 |
| 2008/0222038 A1 | 9/2008 | Eden et al. |
| 2008/0222295 A1 | 9/2008 | Robinson et al. |
| 2008/0228467 A1 | 9/2008 | Womack et al. |
| 2008/0235199 A1 | 9/2008 | Li et al. |
| 2008/0243711 A1 | 10/2008 | Aymeloglu et al. |
| 2008/0249820 A1 | 10/2008 | Pathria et al. |
| 2008/0255973 A1 | 10/2008 | El Wade et al. |
| 2008/0263468 A1 | 10/2008 | Cappione et al. |
| 2008/0267386 A1 | 10/2008 | Cooper |
| 2008/0270316 A1 | 10/2008 | Guidotti et al. |
| 2008/0270438 A1 | 10/2008 | Aronson et al. |
| 2008/0281580 A1 | 11/2008 | Zabokritski |
| 2008/0281819 A1 | 11/2008 | Tenenbaum et al. |
| 2008/0301042 A1 | 12/2008 | Patzer |
| 2008/0313132 A1 | 12/2008 | Hao et al. |
| 2008/0313243 A1 | 12/2008 | Poston et al. |
| 2009/0018996 A1 | 1/2009 | Hunt et al. |
| 2009/0031401 A1 | 1/2009 | Cudich et al. |
| 2009/0043801 A1 | 2/2009 | LeClair et al. |
| 2009/0055208 A1* | 2/2009 | Kaiser ................. G06Q 10/02 705/5 |
| 2009/0055487 A1 | 2/2009 | Moraes et al. |
| 2009/0070162 A1 | 3/2009 | Leonelli et al. |
| 2009/0076845 A1 | 3/2009 | Bellin et al. |
| 2009/0089651 A1 | 4/2009 | Herberger et al. |
| 2009/0094166 A1 | 4/2009 | Aymeloglu et al. |
| 2009/0106178 A1 | 4/2009 | Chu |
| 2009/0106242 A1 | 4/2009 | McGrew et al. |
| 2009/0112678 A1 | 4/2009 | Luzardo |
| 2009/0112745 A1 | 4/2009 | Stefanescu |

(56) References Cited

U.S. PATENT DOCUMENTS

| | | |
|---|---|---|
| 2009/0125359 A1 | 5/2009 | Knapic |
| 2009/0125459 A1 | 5/2009 | Norton et al. |
| 2009/0132953 A1 | 5/2009 | Reed et al. |
| 2009/0150868 A1 | 6/2009 | Chakra et al. |
| 2009/0164387 A1 | 6/2009 | Armstrong et al. |
| 2009/0164934 A1 | 6/2009 | Bhattiprolu et al. |
| 2009/0177492 A1 | 7/2009 | Hasan et al. |
| 2009/0187546 A1 | 7/2009 | Whyte et al. |
| 2009/0187548 A1 | 7/2009 | Ji et al. |
| 2009/0198518 A1 | 8/2009 | McKenzie et al. |
| 2009/0199106 A1 | 8/2009 | Jonsson et al. |
| 2009/0216562 A1* | 8/2009 | Faulkner ............... G06F 19/322 705/2 |
| 2009/0222287 A1 | 9/2009 | Legorreta et al. |
| 2009/0228365 A1 | 9/2009 | Tomchek et al. |
| 2009/0240529 A1 | 9/2009 | Chess et al. |
| 2009/0248757 A1 | 10/2009 | Havewala et al. |
| 2009/0249244 A1 | 10/2009 | Robinson et al. |
| 2009/0271343 A1 | 10/2009 | Vaiciulis et al. |
| 2009/0281839 A1 | 11/2009 | Lynn et al. |
| 2009/0287470 A1 | 11/2009 | Farnsworth et al. |
| 2009/0299830 A1 | 12/2009 | West et al. |
| 2009/0307049 A1 | 12/2009 | Elliott et al. |
| 2009/0313311 A1 | 12/2009 | Hoffmann et al. |
| 2009/0313463 A1 | 12/2009 | Pang et al. |
| 2009/0319418 A1 | 12/2009 | Herz |
| 2009/0319891 A1 | 12/2009 | MacKinlay et al. |
| 2010/0030722 A1 | 2/2010 | Goodson et al. |
| 2010/0031141 A1 | 2/2010 | Summers et al. |
| 2010/0042922 A1 | 2/2010 | Bradateanu et al. |
| 2010/0057622 A1 | 3/2010 | Faith et al. |
| 2010/0070531 A1 | 3/2010 | Aymeloglu et al. |
| 2010/0070842 A1 | 3/2010 | Aymeloglu et al. |
| 2010/0070844 A1 | 3/2010 | Aymeloglu et al. |
| 2010/0070897 A1 | 3/2010 | Aymeloglu et al. |
| 2010/0082369 A1 | 4/2010 | Prenelus et al. |
| 2010/0082541 A1 | 4/2010 | Kottomtharayil |
| 2010/0082671 A1 | 4/2010 | Li et al. |
| 2010/0094765 A1 | 4/2010 | Nandy |
| 2010/0098318 A1 | 4/2010 | Anderson |
| 2010/0114817 A1 | 5/2010 | Gilbert et al. |
| 2010/0114887 A1 | 5/2010 | Conway et al. |
| 2010/0122152 A1 | 5/2010 | Chamberlain et al. |
| 2010/0131502 A1 | 5/2010 | Fordham |
| 2010/0145909 A1 | 6/2010 | Ngo |
| 2010/0161735 A1 | 6/2010 | Sharma |
| 2010/0169192 A1 | 7/2010 | Zoldi et al. |
| 2010/0191563 A1 | 7/2010 | Schlaifer et al. |
| 2010/0204983 A1 | 8/2010 | Chung et al. |
| 2010/0223260 A1 | 9/2010 | Wu |
| 2010/0235915 A1 | 9/2010 | Memon et al. |
| 2010/0262688 A1 | 10/2010 | Hussain et al. |
| 2010/0280851 A1 | 11/2010 | Merkin |
| 2010/0293174 A1 | 11/2010 | Bennett et al. |
| 2010/0306285 A1 | 12/2010 | Shah et al. |
| 2010/0306713 A1 | 12/2010 | Geisner et al. |
| 2010/0312837 A1 | 12/2010 | Bodapati et al. |
| 2010/0313239 A1 | 12/2010 | Chakra et al. |
| 2010/0324929 A1 | 12/2010 | Petrasich et al. |
| 2010/0325581 A1 | 12/2010 | Finkelstein et al. |
| 2011/0004626 A1 | 1/2011 | Naeymi-Rad et al. |
| 2011/0047159 A1 | 2/2011 | Baid et al. |
| 2011/0055074 A1 | 3/2011 | Chen et al. |
| 2011/0060753 A1 | 3/2011 | Shaked et al. |
| 2011/0061013 A1 | 3/2011 | Bilicki et al. |
| 2011/0066497 A1 | 3/2011 | Gopinath et al. |
| 2011/0078173 A1 | 3/2011 | Seligmann et al. |
| 2011/0093327 A1 | 4/2011 | Fordyce et al. |
| 2011/0099133 A1 | 4/2011 | Chang et al. |
| 2011/0099628 A1 | 4/2011 | Lanxner et al. |
| 2011/0131122 A1 | 6/2011 | Griffin et al. |
| 2011/0153384 A1 | 6/2011 | Horne et al. |
| 2011/0161409 A1 | 6/2011 | Nair et al. |
| 2011/0167105 A1 | 7/2011 | Ramakrishnan et al. |
| 2011/0173093 A1 | 7/2011 | Psota et al. |
| 2011/0179048 A1 | 7/2011 | Satlow |
| 2011/0208565 A1 | 8/2011 | Ross et al. |
| 2011/0208724 A1 | 8/2011 | Jones et al. |
| 2011/0208822 A1 | 8/2011 | Rathod |
| 2011/0213655 A1 | 9/2011 | Henkin |
| 2011/0218955 A1 | 9/2011 | Tang |
| 2011/0225482 A1 | 9/2011 | Chan et al. |
| 2011/0225586 A1 | 9/2011 | Bentley et al. |
| 2011/0231305 A1 | 9/2011 | Winters |
| 2011/0246229 A1 | 10/2011 | Pacha |
| 2011/0252282 A1 | 10/2011 | Meek et al. |
| 2011/0258216 A1 | 10/2011 | Supakkul et al. |
| 2011/0270604 A1 | 11/2011 | Qi et al. |
| 2011/0270834 A1 | 11/2011 | Sokolan et al. |
| 2011/0289397 A1 | 11/2011 | Eastmond et al. |
| 2011/0291851 A1 | 12/2011 | Whisenant |
| 2011/0295649 A1 | 12/2011 | Fine |
| 2011/0307382 A1 | 12/2011 | Siegel et al. |
| 2011/0310005 A1 | 12/2011 | Chen et al. |
| 2011/0314007 A1 | 12/2011 | Dassa et al. |
| 2011/0314024 A1 | 12/2011 | Chang et al. |
| 2012/0004894 A1 | 1/2012 | Butler et al. |
| 2012/0011238 A1 | 1/2012 | Rathod |
| 2012/0011245 A1 | 1/2012 | Gillette et al. |
| 2012/0013684 A1 | 1/2012 | Lucia |
| 2012/0019559 A1 | 1/2012 | Siler et al. |
| 2012/0022945 A1 | 1/2012 | Falkenberg et al. |
| 2012/0036434 A1 | 2/2012 | Oberstein |
| 2012/0054284 A1 | 3/2012 | Rakshit |
| 2012/0059853 A1 | 3/2012 | Jagota |
| 2012/0065987 A1* | 3/2012 | Farooq ................. G06F 19/327 705/2 |
| 2012/0066166 A1 | 3/2012 | Curbera et al. |
| 2012/0078595 A1 | 3/2012 | Balandin et al. |
| 2012/0079363 A1 | 3/2012 | Folting et al. |
| 2012/0084117 A1 | 4/2012 | Tavares et al. |
| 2012/0084184 A1 | 4/2012 | Raleigh et al. |
| 2012/0084287 A1 | 4/2012 | Lakshminarayan et al. |
| 2012/0131512 A1 | 5/2012 | Takeuchi et al. |
| 2012/0144335 A1 | 6/2012 | Abeln et al. |
| 2012/0158585 A1 | 6/2012 | Ganti |
| 2012/0159362 A1 | 6/2012 | Brown et al. |
| 2012/0173381 A1 | 7/2012 | Smith |
| 2012/0188252 A1 | 7/2012 | Law |
| 2012/0191446 A1 | 7/2012 | Binsztok et al. |
| 2012/0196558 A1 | 8/2012 | Reich et al. |
| 2012/0197657 A1 | 8/2012 | Prodanovic |
| 2012/0197660 A1 | 8/2012 | Prodanovich |
| 2012/0215784 A1 | 8/2012 | King et al. |
| 2012/0221553 A1 | 8/2012 | Wittmer et al. |
| 2012/0221580 A1 | 8/2012 | Barney |
| 2012/0226523 A1 | 9/2012 | Weiss |
| 2012/0226590 A1 | 9/2012 | Love et al. |
| 2012/0245976 A1 | 9/2012 | Kumar et al. |
| 2012/0246148 A1 | 9/2012 | Dror |
| 2012/0278249 A1 | 11/2012 | Duggal et al. |
| 2012/0310661 A1 | 12/2012 | Greene |
| 2012/0323888 A1 | 12/2012 | Osann, Jr. |
| 2012/0330973 A1 | 12/2012 | Ghuneim et al. |
| 2013/0006655 A1 | 1/2013 | Van Arkel et al. |
| 2013/0006668 A1 | 1/2013 | Van Arkel et al. |
| 2013/0016106 A1 | 1/2013 | Yip et al. |
| 2013/0046842 A1 | 2/2013 | Muntz et al. |
| 2013/0054306 A1 | 2/2013 | Bhalla |
| 2013/0057551 A1 | 3/2013 | Ebert et al. |
| 2013/0061169 A1 | 3/2013 | Pearcy et al. |
| 2013/0073377 A1 | 3/2013 | Heath |
| 2013/0096968 A1 | 4/2013 | Van Pelt et al. |
| 2013/0096988 A1 | 4/2013 | Grossman et al. |
| 2013/0097130 A1 | 4/2013 | Bingol et al. |
| 2013/0097482 A1 | 4/2013 | Marantz et al. |
| 2013/0110746 A1 | 5/2013 | Ahn |
| 2013/0117081 A1 | 5/2013 | Wilkins et al. |
| 2013/0124193 A1 | 5/2013 | Holmberg |
| 2013/0132348 A1 | 5/2013 | Garrod |
| 2013/0151453 A1 | 6/2013 | Bhanot et al. |
| 2013/0166348 A1 | 6/2013 | Scotto |
| 2013/0166480 A1 | 6/2013 | Popsecu et al. |
| 2013/0185245 A1 | 7/2013 | Anderson |

(56) References Cited

U.S. PATENT DOCUMENTS

| | | |
|---|---|---|
| 2013/0185307 A1 | 7/2013 | El-Yaniv et al. |
| 2013/0224696 A1 | 8/2013 | Wolfe et al. |
| 2013/0226318 A1 | 8/2013 | Procyk |
| 2013/0226944 A1 | 8/2013 | Baid et al. |
| 2013/0238616 A1 | 9/2013 | Rose et al. |
| 2013/0238664 A1 | 9/2013 | Hsu et al. |
| 2013/0246170 A1 | 9/2013 | Gross et al. |
| 2013/0246537 A1 | 9/2013 | Gaddala |
| 2013/0246597 A1 | 9/2013 | Iizawa et al. |
| 2013/0208565 A1 | 10/2013 | Castellanos et al. |
| 2013/0262328 A1 | 10/2013 | Federgreen |
| 2013/0262527 A1 | 10/2013 | Hunter et al. |
| 2013/0263019 A1 | 10/2013 | Castellanos et al. |
| 2013/0276799 A1 | 10/2013 | Davidson |
| 2013/0282696 A1 | 10/2013 | John et al. |
| 2013/0290011 A1 | 10/2013 | Lynn et al. |
| 2013/0290825 A1 | 10/2013 | Arndt et al. |
| 2013/0297619 A1 | 11/2013 | Chandrasekaran et al. |
| 2013/0304770 A1 | 11/2013 | Boero et al. |
| 2013/0325826 A1 | 12/2013 | Agarwal et al. |
| 2014/0006404 A1 | 1/2014 | McGrew et al. |
| 2014/0012724 A1 | 1/2014 | O'Leary et al. |
| 2014/0012796 A1 | 1/2014 | Petersen et al. |
| 2014/0019936 A1 | 1/2014 | Cohanoff |
| 2014/0032506 A1 | 1/2014 | Hoey et al. |
| 2014/0033010 A1 | 1/2014 | Richardt et al. |
| 2014/0040371 A1 | 2/2014 | Gurevich et al. |
| 2014/0052466 A1 | 2/2014 | DeVille et al. |
| 2014/0058754 A1 | 2/2014 | Wild |
| 2014/0058763 A1 | 2/2014 | Zizzamia et al. |
| 2014/0058914 A1 | 2/2014 | Song et al. |
| 2014/0068487 A1 | 3/2014 | Steiger et al. |
| 2014/0081652 A1 | 3/2014 | Klindworth |
| 2014/0095363 A1 | 4/2014 | Caldwell |
| 2014/0095509 A1 | 4/2014 | Patton |
| 2014/0108074 A1 | 4/2014 | Miller et al. |
| 2014/0108380 A1 | 4/2014 | Gotz et al. |
| 2014/0108985 A1 | 4/2014 | Scott et al. |
| 2014/0123279 A1 | 5/2014 | Bishop et al. |
| 2014/0129936 A1 | 5/2014 | Richards |
| 2014/0136237 A1 | 5/2014 | Anderson et al. |
| 2014/0136285 A1 | 5/2014 | Carvalho |
| 2014/0143009 A1 | 5/2014 | Brice et al. |
| 2014/0149130 A1 | 5/2014 | Getchius |
| 2014/0156527 A1 | 6/2014 | Grigg et al. |
| 2014/0157172 A1 | 6/2014 | Peery et al. |
| 2014/0164502 A1 | 6/2014 | Khodorenko et al. |
| 2014/0189536 A1 | 7/2014 | Lange et al. |
| 2014/0195515 A1 | 7/2014 | Baker et al. |
| 2014/0214579 A1 | 7/2014 | Shen et al. |
| 2014/0222521 A1 | 8/2014 | Chait |
| 2014/0222752 A1 | 8/2014 | Isman et al. |
| 2014/0222793 A1 | 8/2014 | Sadkin et al. |
| 2014/0229554 A1 | 8/2014 | Grunin et al. |
| 2014/0244284 A1 | 8/2014 | Smith |
| 2014/0278339 A1 | 9/2014 | Aliferis et al. |
| 2014/0278479 A1 | 9/2014 | Wang et al. |
| 2014/0282177 A1 | 9/2014 | Wang et al. |
| 2014/0344230 A1 | 11/2014 | Krause et al. |
| 2014/0358789 A1 | 12/2014 | Boding et al. |
| 2014/0358829 A1 | 12/2014 | Hurwitz |
| 2014/0366132 A1 | 12/2014 | Stiansen et al. |
| 2015/0012509 A1 | 1/2015 | Kirn |
| 2015/0046481 A1 | 2/2015 | Elliot |
| 2015/0073929 A1 | 3/2015 | Psota et al. |
| 2015/0073954 A1 | 3/2015 | Braff |
| 2015/0085997 A1* | 3/2015 | Biage ............... H04M 3/00 379/45 |
| 2015/0095773 A1 | 4/2015 | Gonsalves et al. |
| 2015/0100897 A1 | 4/2015 | Sun et al. |
| 2015/0106379 A1 | 4/2015 | Elliot et al. |
| 2015/0134512 A1 | 5/2015 | Mueller |
| 2015/0135256 A1 | 5/2015 | Hoy et al. |
| 2015/0161611 A1 | 6/2015 | Duke et al. |
| 2015/0186821 A1 | 7/2015 | Wang et al. |
| 2015/0187036 A1 | 7/2015 | Wang et al. |
| 2015/0188872 A1 | 7/2015 | White |
| 2015/0235334 A1 | 8/2015 | Wang et al. |
| 2015/0254220 A1 | 9/2015 | Burr et al. |
| 2015/0269316 A1 | 9/2015 | Hussam |
| 2015/0269334 A1 | 9/2015 | Fendell et al. |
| 2015/0338233 A1 | 11/2015 | Cervelli et al. |
| 2015/0379413 A1 | 12/2015 | Robertson et al. |
| 2016/0004764 A1 | 1/2016 | Chakerian et al. |
| 2016/0034578 A1 | 2/2016 | Wang et al. |

FOREIGN PATENT DOCUMENTS

| | | | |
|---|---|---|---|
| CN | 102054015 | 5/2014 | |
| DE | 102014103476 | 9/2014 | |
| DE | 102014204827 | 9/2014 | |
| DE | 102014204830 | 9/2014 | |
| DE | 102014204834 | 9/2014 | |
| DE | 102014213036 | 1/2015 | |
| EP | 1672527 | 6/2006 | |
| EP | 1840523 B1 * | 3/2011 | ........... G01C 21/362 |
| EP | 2487610 | 8/2012 | |
| EP | 2778913 | 9/2014 | |
| EP | 2778914 | 9/2014 | |
| EP | 2858018 | 4/2015 | |
| EP | 2869211 | 5/2015 | |
| EP | 2889814 | 7/2015 | |
| EP | 2892197 | 7/2015 | |
| EP | 2963595 | 1/2016 | |
| EP | 2980748 | 2/2016 | |
| GB | 2366498 | 3/2002 | |
| GB | 2513472 | 10/2014 | |
| GB | 2513721 | 11/2014 | |
| GB | 2514239 | 11/2014 | |
| GB | 2517582 | 2/2015 | |
| NL | 2013134 | 1/2015 | |
| WO | WO 01/025906 | 4/2001 | |
| WO | WO 01/088750 | 11/2001 | |
| WO | WO 2005/116851 | 12/2005 | |
| WO | WO 2008/113059 | 9/2008 | |
| WO | WO 2009/051987 | 4/2009 | |
| WO | WO 2009/061501 | 5/2009 | |
| WO | WO 2010/030913 | 3/2010 | |
| WO | WO 2010/030914 | 3/2010 | |
| WO | WO 2010/030919 | 3/2010 | |
| WO | WO 2012/119008 | 9/2012 | |

OTHER PUBLICATIONS

"A Real-World Problem of Matching Records," Nov. 2006, http://grupoweb.upf.es/bd-web/slides/ullman.pdf, pp. 1-16.

"A Tour of Pinboard," http://pinboard.in/tour as printed May 15, 2014 in 6 pages.

Abbey, Kristen, "Review of Google Docs," May 1, 2007, pp. 2.

Adams et al., "Worklets: A Service-Oriented Implementation of Dynamic Flexibility in Workflows," R. Meersman, Z. Tari et al. (Eds.): OTM 2006, LNCS, 4275, pp. 291-308, 2006.

Bluttman et al., "Excel Formulas and Functions for Dummies," 2005, Wiley Publishing, Inc., pp. 280, 284-286.

Brandel, Mary, "Data Loss Prevention Dos and Don'ts," http://web.archive.org/web/20080724024847/http://www.csoonline.com/article/221272/Dos_and Don_ts_for_Data_Loss_Prevention, Oct. 10, 2007, pp. 5.

Chaudhuri et al., "An Overview of Business Intelligence Technology," Communications of the ACM, Aug. 2011, vol. 54, No. 8.

Conner, Nancy, "Google Apps: The Missing Manual," May 1, 2008, pp. 15.

Definition "Identify" downloaded Jan. 22, 2015, 1 page.

Definition "Overlay" downloaded Jan. 22, 2015, 1 page.

Delicious, http://delicious.com/ as printed May 15, 2014 in 1 page.

"E-MailRelay," http://web.archive.org/web/20080821175021/http://emailrelay.sourceforge.net/ Aug. 21, 2008, pp. 2.

Galliford, Miles, "SnagIt Versus Free Screen Capture Software: Critical Tools for Website Owners," http://www.subhub.com/articles/free-screen-capture-software. Mar. 27, 2008, pp. 11.

(56) References Cited

OTHER PUBLICATIONS

"GrabUp—What a Timesaver!" http://atlchris.com/191/grabup/, Aug. 11, 2008, pp. 3.
Gu et al., "Record Linkage: Current Practice and Future Directions," Jan. 15, 2004, pp. 32.
Hua et al., "A Multi-attribute Data Structure with Parallel Bloom Filters for Network Services" HiPC 2006, LNCS 4297, pp. 277-288, 2006.
JetScreenshot.com, "Share Screenshots via Internet in Seconds," http://web.archive.org/web/20130807164204/http://www.jetscreenshot.com/, Aug. 7, 2013, pp. 1.
Johnson, Maggie, "Introduction to YACC and Bison", CS143, Handout 13, Jul. 8, 2005, pp. 11.
Johnson, Steve, "Access 2013 on Demand", May 9, 2013, Que Publishing.
Kwout, http://web.archive.org/web/20080905132448/http://www.kwout.com/ Sep. 5, 2008, pp. 2.
Lim et al., "Resolving Attribute Incompatibility in Database Integration: An Evidential Reasoning Approach," Department of Computer Science, University of Minnesota, 1994, http://reference.kfupm.edu.sa/content/r/e/resolving_attribute_incompatibility_in_d_531691.pdf, pp. 1-10.
Litwin et al., "Multidatabase Interoperability," IEEE Computer, Dec. 1986, vol. 19, No. 12, http://www.lamsade.dauphine.fr/~litwin/mdb-interoperability.pdf, pp. 10-18.
Madden, Tom, "Chapter 16: The BLAST Sequence Analysis Tool," The NCBI Handbook, Oct. 2002, pp. 1-15.
Microsoft, "Registering an Application to a URI Scheme," http://msdn.microsoft.com/en-us/library/aa767914.aspx, printed Apr. 4, 2009 in 4 pages.
Microsoft, "Using the Clipboard," http://msdn.microsoft.com/en-us/library/ms649016.aspx, printed Jun. 8, 2009 in 20 pages.
Microsoft Windows, "Microsoft Windows Version 2002 Print Out 2," 2002, pp. 1-6.
Nadeau et al., "A Survey of Named Entity Recognition and Classification," Jan. 15, 2004, pp. 20.
Nin et al., "On the Use of Semantic Blocking Techniques for Data Cleansing and Integration," 11th International Database Engineering and Applications Symposium, 2007, pp. 9.
Nitro, "Trick: How to Capture a Screenshot as PDF, Annotate, Then Share It," http://blog.nitropdf.com/2008/03/04/trick-how-to-capture-a-screenshot-as-pdf-annotate-it-then-share/, Mar. 4, 2008, pp. 2.
Online Tech Tips, "Clip2Net—Share files, folders and screenshots easily," https://www.online-tech-tips.com/free-software-downloads/share-files-folders-screenshots/, Apr. 2, 2008, pp. 5.
O'Reilly.com, http://oreilly.com/digitalmedia/2006/01/01/mac-os-x-screenshot-secrets.html, published Jan. 1, 2006 in 10 pages.
Pythagoras Communications Ltd., "Microsoft CRM Duplicate Detection," Sep. 13, 2011, https://www.youtube.com/watch?v=j-7Qis0D0Kc.
Qiang et al., "A Mutual-Information-Based Approach to Entity Reconciliation in Heterogeneous Databases," Proceedings of 2008 International Conference on Computer Science & Software Engineering, IEEE Computer Society, New York, NY, Dec. 12-14, 2008, pp. 666-669.
Schroder, Stan, "15 Ways to Create Website Screenshots," http://mashable.com/2007/08/24/web-screenshots/, Aug. 24, 22007, pp. 2.
Sekine et al., "Definition, Dictionaries and Tagger for Extended Named Entity Hierarchy," May 2004, pp. 1977-1980.
SnagIt, "SnagIt Online Help Guide," http://download.techsmith.com/snagit/docs/onlinehelp/enu/snagit_help.pdf, TechSmith Corp., Version 8.1 printed Feb. 7, 2007, pp. 284.
SnagIt, "SnagIt 8.1.0 Print Out," Software release date Jun. 15, 2006, pp. 6.
SnagIt, "SnagIt 8.1.0 Print Out 2," Software release date Jun. 15, 2006, pp. 1-3.
Wang et al., "Research on a Clustering Data De-Duplication Mechanism Based on Bloom Filter," IEEE 2010, 5 pages.
Warren, Christina, "TUAW Faceoff: Screenshot apps on the firing line," http://www.tuaw.com/2008/05/05/tuaw-faceoff-screenshot-apps-on-the-firing-line-/, May 5, 2008, pp. 11.
Wikipedia, "Multimap," Jan. 1, 2013, https://en.wikipedia.org/w/index.php?title=Multimap&oldid=530800748.
Zhao et al., "Entity Matching Across Heterogeneous Data Sources: An Approach Based on Constrained Cascade Generalization," Data & Knowledge Engineering, vol. 66, No. 3, Sep. 2008, pp. 368-381.
European Search Report for European Patent Application No. 09813700.3 dated Apr. 3, 2014.
Extended European Search Report for European Patent Application No. 14158958.0 dated Jun. 3, 2014.
Extended European Search Report for European Patent Application No. 14158977.0 dated Jun. 10, 2014.
Notice of Acceptance for Australian Patent Application No. 2013251186 dated Nov. 6, 2015.
Notice of Allowance for U.S. Appl. No. 12/556,307 dated Jan. 4, 2016.
Notice of Allowance for U.S. Appl. No. 14/265,637 dated Feb. 13, 2015.
Notice of Allowance for U.S. Appl. No. 14/304,741 dated Apr. 7, 2015.
Notice of Allowance for U.S. Appl. No. 14/552,336 dated Nov. 3, 2015.
Official Communication for Australian Patent Application No. 2013251186 dated Mar. 12, 2015.
Official Communication for Australian Patent Application No. 2014201506 dated Feb. 27, 2015.
Official Communication for Australian Patent Application No. 2014201507 dated Feb. 27, 2015.
Official Communication for Australian Patent Application No. 2014203669 dated May 29, 2015.
Official Communication for Canadian Patent Application No. 2831660 dated Jun. 9, 2015.
Official Communication for European Patent Application No. 12181585.6 dated Sep. 4, 2015.
Official Communication for European Patent Application No. 14158958.0 dated Apr. 16, 2015.
Official Communication for European Patent Application No. 14158977.0 dated Apr. 16, 2015.
Official Communication for European Patent Application No. 15156004.2 dated Aug. 24, 2015.
Official Communication for European Patent Application No. 15179122.5 dated Sep. 11, 2015.
Official Communication for Great Britain Patent Application No. 1404486.1 dated May 21, 2015.
Official Communication for Great Britain Patent Application No. 1404486.1 dated Aug. 27, 2014.
Official Communication for Great Britain Patent Application No. 1404489.5 dated May 21, 2015.
Official Communication for Great Britain Patent Application No. 1404489.5 dated Aug. 27, 2014.
Official Communication for Great Britain Patent Application No. 1404499.4 dated Jun. 11, 2015.
Official Communication for Great Britain Patent Application No. 1404499.4 dated Aug. 20, 2014.
Official Communication for Great Britain Patent Application No. 1404573.6 dated Sep. 10, 2014.
Official Communication for Great Britain Patent Application No. 1411984.6 dated Dec. 22, 2014.
Official Communication for Netherlands Patent Application No. 2011729 dated Aug. 13, 2015.
Official Communication for Netherlands Patent Application No. 2012438 dated Sep. 21, 2015.
Official Communication for Netherlands Patent Application No. 2013134 dated Apr. 20, 2015.
Official Communication for Netherlands Patents Application No. 2012417 dated Sep. 18, 2015.
Official Communication for Netherlands Patents Application No. 2012421 dated Sep. 18, 2015.
Official Communication for New Zealand Patent Application No. 622389 dated Mar. 20, 2014.

(56) References Cited

OTHER PUBLICATIONS

Official Communication for New Zealand Patent Application No. 622404 dated Mar. 20, 2014.
Official Communication for New Zealand Patent Application No. 622439 dated Mar. 24, 2014.
Official Communication for New Zealand Patent Application No. 622439 dated Jun. 6, 2014.
Official Communication for New Zealand Patent Application No. 622473 dated Jun. 19, 2014.
Official Communication for New Zealand Patent Application No. 622473 dated Mar. 27, 2014.
Official Communication for New Zealand Patent Application No. 628161 dated Aug. 25, 2014.
Official Communication for U.S. Appl. No. 12/556,307 dated Oct. 1, 2013.
Official Communication for U.S. Appl. No. 12/556,307 dated Feb. 13, 2012.
Official Communication for U.S. Appl. No. 12/556,307 dated Mar. 14, 2014.
Official Communication for U.S. Appl. No. 12/556,307 dated Sep. 2, 2011.
Official Communication for U.S. Appl. No. 12/556,307 dated Jun. 9, 2015.
Official Communication for U.S. Appl. No. 12/556,321 dated Jun. 6, 2012.
Official Communication for U.S. Appl. No. 12/556,321 dated Dec. 7, 2011.
Official Communication for U.S. Appl. No. 12/556,321 dated Jul. 7, 2015.
Official Communication for U.S. Appl. No. 13/669,274 dated Aug. 26, 2015.
Official Communication for U.S. Appl. No. 13/669,274 dated May 6, 2015.
Official Communication for U.S. Appl. No. 13/827,491 dated Dec. 1, 2014.
Official Communication for U.S. Appl. No. 13/827,491 dated Jun. 22, 2015.
Official Communication for U.S. Appl. No. 13/827,491 dated Oct. 9, 2015.
Official Communication for U.S. Appl. No. 13/831,791 dated Mar. 4, 2015.
Official Communication for U.S. Appl. No. 13/831,791 dated Aug. 6, 2015.
Official Communication for U.S. Appl. No. 13/835,688 dated Jun. 17, 2015.
Official Communication for U.S. Appl. No. 13/835,688 dated Sep. 30, 2015.
Official Communication for U.S. Appl. No. 13/949,043 dated Jan. 15, 2016.
Official Communication for U.S. Appl. No. 13/949,043 dated Oct. 15, 2013.
Official Communication for U.S. Appl. No. 13/949,043 dated May 7, 2015.
Official Communication for U.S. Appl. No. 14/014,313 dated Jun. 18, 2015.
Official Communication for U.S. Appl. No. 14/170,562 dated Jul. 17, 2015.
Official Communication for U.S. Appl. No. 14/170,562 dated Mar. 19, 2014.
Official Communication for U.S. Appl. No. 14/170,562 dated Oct. 2, 2015.
Official Communication for U.S. Appl. No. 14/170,562 dated Sep. 25, 2014.
Official Communication for U.S. Appl. No. 14/222,364 dated Dec. 9, 2015.
Official Communication for U.S. Appl. No. 14/265,637 dated Sep. 26, 2014.
Official Communication for U.S. Appl. No. 14/289,596 dated Jul. 18, 2014.
Official Communication for U.S. Appl. No. 14/289,596 dated Jan. 26, 2015.
Official Communication for U.S. Appl. No. 14/289,596 dated Apr. 30, 2015.
Official Communication for U.S. Appl. No. 14/289,599 dated Jul. 22, 2014.
Official Communication for U.S. Appl. No. 14/289,599 dated May 29, 2015.
Official Communication for U.S. Appl. No. 14/289,599 dated Sep. 4, 2015.
Official Communication for U.S. Appl. No. 14/304,741 dated Mar. 3, 2015.
Official Communication for U.S. Appl. No. 14/304,741 dated Aug. 6, 2014.
Official Communication for U.S. Appl. No. 14/449,083 dated Mar. 12, 2015.
Official Communication for U.S. Appl. No. 14/449,083 dated Oct. 2, 2014.
Official Communication for U.S. Appl. No. 14/449,083 dated Aug. 26, 2015.
Official Communication for U.S. Appl. No. 14/518,757 dated Dec. 1, 2015.
Official Communication for U.S. Appl. No. 14/518,757 dated Apr. 2, 2015.
Official Communication for U.S. Appl. No. 14/518,757 dated Jul. 20, 2015.
Official Communication for U.S. Appl. No. 14/552,336 dated Jul. 20, 2015.
Official Communication for U.S. Appl. No. 14/571,098 dated Nov. 10, 2015.
Official Communication for U.S. Appl. No. 14/571,098 dated Mar. 11, 2015.
Official Communication for U.S. Appl. No. 14/571,098 dated Aug. 24, 2015.
Official Communication for U.S. Appl. No. 14/571,098 dated Aug. 5, 2015.
Official Communication for U.S. Appl. No. 14/800,447 dated Dec. 10, 2015.
Official Communication for U.S. Appl. No. 14/842,734 dated Nov. 19, 2015.
Official Communication for U.S. Appl. No. 15/181,712 dated Nov. 14, 2018.
Acklen, Laura, "Absolute Beginner's Guide to Microsoft Word 2003," Dec. 24, 2003, pp. 15-18, 34-41, 308-316.
Amnet, "5 Great Tools for Visualizing Your Twitter Followers," posted Aug. 4, 2010, http://www.amnetblog.com/component/content/article/115-5-grate-tools-for-visualizing-your-twitter-followers.html.
Ananiev et al., "The New Modality API," http://web.archive.org/web/20061211011958/http://java.sun.com/developer/technicalArticles/J2SE/Desktop/javase6/modality/ Jan. 21, 2006, pp. 8.
Appacts, "Smart Thinking for Super Apps," <http://www.appacts.com> Printed Jul. 18, 2013 in 4 pages.
Apsalar, "Data Powered Mobile Advertising," "Free Mobile App Analytics" and various analytics related screen shots <http://apsalar.com> Printed Jul. 18, 2013 in 8 pages.
Bugzilla@Mozilla, "Bug 18726—[feature] Long-click means of invoking contextual menus not supported," http://bugzilla.mozilla.org/show_bug.cgi?id=18726 printed Jun. 13, 2013 in 11 pages.
Capptain—Pilot Your Apps, <http://www.capptain.com> Printed Jul. 18, 2013 in 6 pages.
Celik, Tantek, "CSS Basic User Interface Module Level 3 (CSS3 UI)," Section 8 Resizing and Overflow, Jan. 17, 2012, retrieved from internet http://www.w3.org/TR/2012/WD-css3-ui-20120117/#resizing-amp-overflow retrieved on May 18, 2015.
Chen et al., "Bringing Order to the Web: Automatically Categorizing Search Results," CHI 2000, Proceedings of the SIGCHI conference on Human Factors in Computing Systems, Apr. 1-6, 2000, The Hague, The Netherlands, pp. 145-152.
Cohn, et al., "Semi-supervised clustering with user feedback," Constrained Clustering: Advances in Algorithms, Theory, and Applications 4.1 (2003): 17-32.

(56) References Cited

OTHER PUBLICATIONS

Countly Mobile Analytics, <http://count.ly/> Printed Jul. 18, 2013 in 9 pages.
Distimo—App Analytics, <http://www.distimo.com/app-analytics> Printed Jul. 18, 2013 in 5 pages.
Dramowicz, Ela, "Retail Trade Area Analysis Using the Huff Model," Directions Magazine, Jul. 2, 2005 in 10 pages, http://www.directionsmag.com/articles/retail-trade-area-analysis-using-the-huff-model/123411.
Flurry Analytics, <http://www.flurry.com/> Printed Jul. 18, 2013 in 14 pages.
GIS-NET 3 Public _ Department of Regional Planning. Planning & Zoning Information for Unincorporated LA County. Retrieved Oct. 2, 2013 from http://gis.planning.lacounty.gov/GIS-NET3_Public/Viewer.html.
Google Analytics Official Website—Web Analytics & Reporting, <http://www.google.com/analytics.index.html> Printed Jul. 18, 2013 in 22 pages.
Gorr et al., "Crime Hot Spot Forecasting: Modeling and Comparative Evaluation", Grant 98-IJ-CX-K005, May 6, 2002, 37 pages.
Griffith, Daniel A., "A Generalized Huff Model," Geographical Analysis, Apr. 1982, vol. 14, No. 2, pp. 135-144.
Hansen et al., "Analyzing Social Media Networks with NodeXL: Insights from a Connected World", Chapter 4, pp. 53-67 and Chapter 10, pp. 143-164, published Sep. 2010.
Hibbert et al., "Prediction of Shopping Behavior Using a Huff Model Within a GIS Framework," Healthy Eating in Context, Mar. 18, 2011, pp. 16.
Huff et al., "Calibrating the Huff Model Using ArcGIS Business Analyst," ESRI, Sep. 2008, pp. 33.
Huff, David L., "Parameter Estimation in the Huff Model," ESRI, ArcUser, Oct.-Dec. 2003, pp. 34-36.
"HunchLab: Heat Map and Kernel Density Calculation for Crime Analysis," Azavea Journal, printed from www.azavea.com/blogs/newsletter/v4i4/kernel-density-capabilities-added-to-hunchlab/ on Sep. 9, 2014, 2 pages.
Keylines.com, "An Introduction to KeyLines and Network Visualization," Mar. 2014, <http://keylines.com/wp-content/uploads/2014/03/KeyLines-White-Paper.pdf> downloaded May 12, 2014 in 8 pages.
Keylines.com, "KeyLines Datasheet," Mar. 2014, <http://keylines.com/wp-content/uploads/2014/03/KeyLines-datasheet.pdf> downloaded May 12, 2014 in 2 pages.
Keylines.com, "Visualizing Threats: Improved Cyber Security Through Network Visualization," Apr. 2014, <http://keylines.com/wp-content/uploads/2014/04/Visualizing-Threats1.pdf> downloaded May 12, 2014 in 10 pages.
Kontagent Mobile Analytics, <http://www.kontagent.com/> Printed Jul. 18, 2013 in 9 pages.
Liu, Tianshun, "Combining GIS and the Huff Model to Analyze Suitable Locations for a New Asian Supermarket in the Minneapolis and St. Paul, Minnesota USA," Papers in Resource Analysis, 2012, vol. 14, pp. 8.
Localytics—Mobile App Marketing & Analytics, <http://www.localytics.com/> Printed Jul. 18, 2013 in 12 pages.
Manno et al., "Introducing Collaboration in Single-user Applications through the Centralized Control Architecture," 2010, pp. 10.
Manske, "File Saving Dialogs," <http://www.mozilla.org/editor/ui_specs/FileSaveDialogs.html>, Jan. 20, 1999, pp. 7.
Map of San Jose, CA. Retrieved Oct. 2, 2013 from http://maps.yahoo.com.
Map of San Jose, CA. Retrieved Oct. 2, 2013 from http://maps.bing.com.
Map of San Jose, CA. Retrieved Oct. 2, 2013 from http://maps.google.com.
Microsoft—Developer Network, "Getting Started with VBA in Word 2010," Apr. 2010, <http://msdn.microsoft.com/en-us/library/ff604039%28v=office.14%29.aspx> as printed Apr. 4, 2014 in 17 pages.

Microsoft Office—Visio, "About connecting shapes," <http://office.microsoft.com/en-us/visio-help/about-connecting-shapes-HP085050369.aspx> printed Aug. 4, 2011 in 6 pages.
Microsoft Office—Visio, "Add and glue connectors with the Connector tool," <http://office.microsoft.com/en-us/visio-help/add-and-glue-connectors-with-the-connector-tool-HA010048532.aspx?CTT=1> printed Aug. 4, 2011 in 1 page.
Mixpanel—Mobile Analytics, <https://mixpanel.com/> Printed Jul. 18, 2013 in 13 pages.
Open Web Analytics (OWA), <http://www.openwebanalytics.com/> Printed Jul. 19, 2013 in 5 pages.
Piwik—Free Web Analytics Software, <http://piwik.org/> Printed Jul. 19, 2013 in 18 pages.
"Refresh CSS Ellipsis When Resizing Container—Stack Overflow," Jul. 31, 2013, retrieved from internet http://stackoverflow.com/questions/17964681/refresh-css-ellipsis-when-resizing-container, retrieved on May 18, 2015.
Sigrist, et al., "Prosite, a Protein Domain Database for Functional Characterization and Annotation," Nucleic Acids Research, 2010, vol. 38, pp. D161-D166.
StatCounter—Free Invisible Web Tracker, Hit Counter and Web Stats, <http://statcounter.com/> Printed Jul. 19, 2013 in 17 pages.
TestFlight—Beta Testing On The Fly, <http://testflightapp.com/> Printed Jul. 18, 2013 in 3 pages.
Trak.io, <http://trak.io/> printed Jul. 18, 2013 in 3 pages.
UserMetrix, <http://usermetrix.com/android-analytics> printed Jul. 18, 2013 in 3 pages.
Valentini et al., "Ensembles of Learning Machines", M. Marinaro and R. Tagliaferri (Eds.): Wirn Vietri 2002, LNCS 2486, pp. 3-20.
Vose et al., "Help File for ModelRisk Version 5," 2007, Vose Software, pp. 349-353. [Uploaded in 2 Parts].
International Search Report and Written Opinion in Application No. PCT/US2009/056703 dated Mar. 15, 2010.
Notice of Allowance for U.S. Appl. No. 14/222,364 dated Jul. 27, 2017.
Notice of Allowance for U.S. Appl. No. 14/225,084 dated May 4, 2015.
Notice of Allowance for U.S. Appl. No. 14/319,161 dated May 4, 2015.
Notice of Allowance for U.S. Appl. No. 14/323,935 dated Oct. 1, 2015.
Notice of Allowance for U.S. Appl. No. 14/479,863 dated Mar. 31, 2015.
Notice of Allowance for U.S. Appl. No. 14/746,671 dated Jan. 21, 2016.
Notice of Allowance for U.S. Appl. No. 14/805,313 dated Jun. 15, 2016.
Notice of Allowance for U.S. Appl. No. 14/923,364 dated May 6, 2016.
Official Communication for European Patent Application No. 14187996.5 dated Feb. 12, 2015.
Official Communication for European Patent Application No. 14191540.5 dated May 27, 2015.
Official Communication for European Patent Application No. 14200246.8 dated May 29, 2015.
Official Communication for European Patent Application No. 14200298.9 dated May 13, 2015.
Official Communication for European Patent Application No. 15181419.1 dated Sep. 29, 2015.
Official Communication for European Patent Application No. 15184764.7 dated Dec. 14, 2015.
Official Communication for Netherlands Patent Application No. 2012421 dated Sep. 18, 2015.
Official Communication for New Zealand Patent Application No. 622513 dated Apr. 3, 2014.
Official Communication for New Zealand Patent Application No. 624557 dated May 14, 2014.
Official Communication for U.S. Appl. No. 13/827,491 dated Mar. 30, 2016.
Official Communication for U.S. Appl. No. 13/831,791 dated Feb. 11, 2016.
Official Communication for U.S. Appl. No. 13/835,688 dated Jun. 7, 2016.

(56) References Cited

OTHER PUBLICATIONS

Official Communication for U.S. Appl. No. 14/141,252 dated Oct. 8, 2015.
Official Communication for U.S. Appl. No. 14/170,562 dated Mar. 3, 2016.
Official Communication for U.S. Appl. No. 14/222,364 dated Jun. 24, 2016.
Official Communication for U.S. Appl. No. 14/225,006 dated Sep. 10, 2014.
Official Communication for U.S. Appl. No. 14/225,006 dated Sep. 2, 2015.
Official Communication for U.S. Appl. No. 14/225,006 dated Dec. 21, 2015.
Official Communication for U.S. Appl. No. 14/225,006 dated Feb. 27, 2015.
Official Communication for U.S. Appl. No. 14/225,084 dated Sep. 11, 2015.
Official Communication for U.S. Appl. No. 14/225,084 dated Sep. 2, 2014.
Official Communication for U.S. Appl. No. 14/225,084 dated Feb. 20, 2015.
Official Communication for U.S. Appl. No. 14/225,084 dated Jan. 4, 2016.
Official Communication for U.S. Appl. No. 14/225,160 dated Feb. 11, 2015.
Official Communication for U.S. Appl. No. 14/225,160 dated Aug. 12, 2015.
Official Communication for U.S. Appl. No. 14/225,160 dated May 20, 2015.
Official Communication for U.S. Appl. No. 14/225,160 dated Oct. 22, 2014.
Official Communication for U.S. Appl. No. 14/225,160 dated Jul. 29, 2014.
Official Communication for U.S. Appl. No. 14/289,596 dated May 9, 2016.
Official Communication for U.S. Appl. No. 14/306,138 dated Dec. 24, 2015.
Official Communication for U.S. Appl. No. 14/306,138 dated Dec. 3, 2015.
Official Communication for U.S. Appl. No. 14/306,147 dated Dec. 24, 2015.
Official Communication for U.S. Appl. No. 14/319,161 dated Jan. 23, 2015.
Official Communication for U.S. Appl. No. 14/449,083 dated Apr. 8, 2016.
Official Communication for U.S. Appl. No. 14/451,221 dated Oct. 21, 2014.
Official Communication for U.S. Appl. No. 14/463,615 dated Sep. 10, 2015.
Official Communication for U.S. Appl. No. 14/463,615 dated Nov. 13, 2014.
Official Communication for U.S. Appl. No. 14/463,615 dated May 21, 2015.
Official Communication for U.S. Appl. No. 14/463,615 dated Jan. 28, 2015.
Official Communication for U.S. Appl. No. 14/463,615 dated Dec. 9, 2015.
Official Communication for U.S. Appl. No. 14/479,863 dated Dec. 26, 2014.
Official Communication for U.S. Appl. No. 14/483,527 dated Jun. 22, 2015.
Official Communication for U.S. Appl. No. 14/483,527 dated Jan. 28, 2015.
Official Communication for U.S. Appl. No. 14/483,527 dated Oct. 28, 2015.
Official Communication for U.S. Appl. No. 14/516,386 dated Feb. 24, 2016.
Official Communication for U.S. Appl. No. 14/562,524 dated Nov. 10, 2015.
Official Communication for U.S. Appl. No. 14/562,524 dated Sep. 14, 2015.
Official Communication for U.S. Appl. No. 14/631,633 dated Sep. 10, 2015.
Official Communication for U.S. Appl. No. 14/676,621 dated Oct. 29, 2015.
Official Communication for U.S. Appl. No. 14/676,621 dated Jul. 30, 2015.
Official Communication for U.S. Appl. No. 14/746,671 dated Nov. 12, 2015.
Official Communication for U.S. Appl. No. 14/805,313 dated Dec. 30, 2015.
Official Communication for U.S. Appl. No. 14/813,749 dated Sep. 28, 2015.
Official Communication for U.S. Appl. No. 14/923,374 dated Feb. 9, 2016.
Official Communication for U.S. Appl. No. 14/958,855 dated May 4, 2016.
Official Communication for U.S. Appl. No. 15/017,324 dated Apr. 22, 2016.
Official Communication for U.S. Appl. No. 15/181,712 dated Jul. 5, 2017.
Official Communication for U.S. Appl. No. 15/181,712 dated Oct. 12, 2016.
Official Communication for U.S. Appl. No. 15/181,712 dated May 2, 2018.
"A First Look: Predicting Market Demand for Food Retail using a Huff Analysis," TRF Policy Solutions, Jul. 2012, pp. 30.
Official Communication for U.S. Appl. No. 14/289,596 dated Aug. 5, 2015.
Official Communication for U.S. Appl. No. 14/518,757 dated Dec. 10, 2014.

* cited by examiner

300 —

JOE SMITH
152467896
Care Team Lead: Jane Doe

Search by name, ID, or SSN... — 204

202

CREATE REPORT — 302

Last updated: 8/15/14

Profile
Edit

| | | |
|---|---|---|
| Birthdate | Primary Phone (Mobile) | Age |
| 07/01/00 | (206) 555-5555 | 14 |

| | | |
|---|---|---|
| Address | Email | Language Eligibility |
| 151 Acres Ln | joe.smith@email.com | English |
| 3 mo. at this address | | ✓ 1/1/14 – present |

Care Type
Foster-Kinship

2 Notifications/Alerts

| | |
|---|---|
| 8/15/14 | Missed Service: Asthma Meds Review |
| 9/15/14 | Upcoming: PCP Appt. Health Assess. |

Fun Facts
Nickname Joey
Food Pizza and Italian
Hobby Soccer
+Add Fun Fact

Medical Snapshot
Edit

Medical Cohorts
Foster Care as of 1/1/14
Asthmatic as of 2/12/10
Mood Disorder as of 7/3/13

Immunizations
Hep B #2 7/03/00
Hep B #1 7/24/00

Current Medications
Medicine #1

Allergies
None
View Complete Medical History

Contacts
Edit

| Care Team | Providers | State Contacts | Foster Guardian |
|---|---|---|---|
| Assigned PCP | Most Seen PCP | Last Seen Specialist | |
| Dr. James Doe | Dr. Peter Doe | Dr. Diane Doe | |
| Family Medicine | Family Medicine | Endocrinologist | |
| 123 Main St | 456 Main St | 789 Main St | |
| Distance: 3.7 mi | Distance: 1.2 mi | Distance: 0.5 mi | |

Prior Authorizations
Edit

| Auth ID | Auth Status | Auth Template | Start Date | Refer from provider |
|---|---|---|---|---|
| 4534634 | Approved | Authorization/Home Health Services (101) | 08/10/14 | Smith, John |
| | | | End Date | Refer to provider |
| | | | 11/10/14 | Johnson, John |

JOE SMITH
152467896
Care Team Lead: Jane Doe

Medical Profile — Edit

Medical Cohorts
Foster Care as of 1/1/14
Asthmatic as of 2/12/10
Mood Disorder as of 7/3/13

Height 5'8"
Weight 180 lbs.

MedAl Risk Score 57

Medications

Medicine #1 – 120mcg

Last Filled 7/3/14
ABC Pharmacy

Prescriber 7/3/14
Dr. Doe

Lab Results

4/20/14 Lab Results One — More
4/20/14 Lab Results Two — More
4/20/14 Lab Results Three — More
4/20/14 Lab Results Four — More
4/20/14 Lab Results Five Search by name, ID, or SSN... — 204 / 202

CARE PLANS — 402
HEALTH ASSESSMENTS — 404

Visits

4/20/14 Psychiatric Evaluation
Psychometric tests and evaluation of behavioral / learning disorder. More

4/15/14 Acute Respiratory Distress
Continuous inhalation treatment with aerosol medication for acute airway obstruction. More

Allergies

Substance — Reaction
Penicillin Compounds — Anaphylaxis

Immunizations

7/30/00 Hep B #2 — More
7/24/00 Hep B #1 — More 212, 214, 216, 218, 220, 222, 224

FIG. 5

JOE SMITH
152467896
Care Team Lead: Jane Doe

Search by name, ID, or SSN...

RECORD VITAL SIGNS

CARE PLAN for JOE SMITH 152467896

Milestones (grouped by goal)
Goal: *Enrollee is referred to resources appropriate to their condition and their ability to self-manage*

| | Type | Care Coordinator | Due Date |
|---|---|---|---|
| | Short Term | Jane Doe | 9/14/2014 |
| Care coordinator to educate enrollee on locating a care giver through available community resources | Intervention | Jane Doe | 9/14/2014 |
| Enrollee takes advantage of resources as a result of Care Coordinator referrals | Outcome | Jane Doe | 9/14/2014 |

Goal: *Enrollee's care will be coordinated between all disciplines*

| | Long Term | Jane Doe | 11/13/2014 |
|---|---|---|---|
| Care coordinator will coordinate all aspects of enrollee's care | Intervention | Jane Doe | 11/13/2014 |
| Enrollee's Care Plan reflects Care Coordination | Outcome | Jane Doe | 11/13/2013 |

212, 214, 216, 218, 220, 222, 224
500, 502, 204, 202

600

JOE SMITH
152467896
Care Team Lead: Jane Doe

Assessments

| Date | Name | Key Results | Recommendations | Status |
|------|------|-------------|-----------------|--------|
| 4/8/13 | GAIN-SS | Social withdrawal Feelings of sadness | Cognitive Behavioral Therapy | Commenced |
| 8/3/11 | PCS-17 | High risk for attention deficit disorder | Pharmacotherapy | Active Rx |

View

Search by name, ID, or SSN...

RECORD VITAL SIGNS

JOE SMITH
152467896
Care Team Lead: Jane Doe

Search by name, ID, or SSN...

700
204
202

7/4/2014
Body Temperature 98.6
Pulse Rate 80
Respiratory Rate 18
Blood Pressure 120/80
Additional notes go here 6/9/2014
Body Temperature 99.6
Pulse Rate 90
Respiratory Rate 18
Blood Pressure 120/80
Additional notes go here 5/3/2014
Body Temperature 98.6
Pulse Rate 85
Respiratory Rate 19
Blood Pressure 130/75
Additional notes go here 4/21/2014
Body Temperature 98.6
Pulse Rate 80
Respiratory Rate 18
Blood Pressure 120/80
Additional notes go here 3/3/2014
Body Temperature 99.0
Pulse Rate 87
Respiratory Rate 16
Blood Pressure 115/83
Additional notes go here 212
214
216
218
220
222
224

Top Diagnoses

| | | Claims | | Unique Visits | | Total Paid | |
|---|---|---|---|---|---|---|---|
| ICD9 Code | Diagnoses | Since 1/2013 | Since 1/2014 | Since 1/2013 | Since 1/2014 | Since 1/2013 | Since 1/2014 |
| 78650 | Chest pain | 7832 | 1989 | 7253 | 1879 | 3.028M | 791,487.72 |
| 78659 | Other chest pain | 4484 | 1179 | 4021 | 1091 | 2.888M | 827,036.81 |
| 51881 | Acute Resp. fail. | 342 | 103 | 297 | 87 | 2.982M | 666,753.97 |
| 28262 | Hb-SS disease | 1703 | 475 | 1562 | 442 | 1.939M | 421,469.64 |

Top Facilities

| | Claims | | Unique Visits | | Total Paid | |
|---|---|---|---|---|---|---|
| Facility | Since 1/2013 | Since 1/2014 | Since 1/2013 | Since 1/2014 | Since 1/2013 | Since 1/2014 |
| Facility 1 | 180 | 56 | 159 | 48 | 8,536.01 | 2,812.95 |
| Facility 2 | 179 | 46 | 159 | 41 | 10,921.24 | 2,668.22 |
| Facility 3 | 125 | 32 | 120 | 32 | 8,385.83 | 2,125.54 |
| Facility 4 | 120 | 30 | 116 | 30 | 49,189.71 | 14,169 |

FIG. 10

UNIFIED DATA INTERFACE AND SYSTEM

TECHNICAL FIELD

The present disclosure relates to systems and techniques for data integration, analysis, and visualization.

BACKGROUND

Physical institutions are available to help vulnerable populations, such as foster children, institutionalized patients, those with behavioral health concerns, the homeless, and/or the like. For example, the foster care system provides various wards, group homes, and/or private homes for minors who can no longer live with their biological parents or guardians. As another example, homeless shelters and soup kitchens offer temporary housing and food for those in need. Often, minors in the foster care system may be placed in multiple foster homes within a short period of time (e.g., less than a year) before they find a permanent residence. Similarly, the homeless may pass between different homeless shelters within a short period of time. The same may be true for members of other vulnerable populations as well. Thus, information about a member of a vulnerable population may be lost during this transitory period.

SUMMARY

The systems, methods, and devices described herein each have several aspects, no single one of which is solely responsible for its desirable attributes. Without limiting the scope of this disclosure, several non-limiting features will now be discussed briefly.

As described above, members of vulnerable populations may transition between different locations. As these members transition between locations, important information about the member may be lost. For example, a minor's medical history, hobbies, interests, and/or the like may be lost if the information is not relayed to the guardians of a new foster home. For the medical history in particular, healthcare providers (e.g., physicians, specialists, pharmacists, etc.) often keep detailed records about a patient. However, if the minor transitions from one foster home in a first geographic area to a second foster home in a second geographic area, one or more of the minor's healthcare providers may change. Even if the minor's healthcare records are transferred from an old healthcare provider to a new healthcare provider, such transfers may leave out important information that another healthcare provider knows about the minor. For example, health information related to the minor may be stored in separate databases (e.g., a claims history may be stored in one database, prescription information may be stored in another database, etc.). The separate databases may not be linked or integrated in any way to allow communication of this information among various healthcare providers. Thus, a minor's old pharmacist may be aware of certain medication that the minor is taking, but this information may not be relayed to a new primary care physician. Likewise, information that is helpful for building rapport between a minor and new health professionals (e.g., hobbies, interests and other social factors) is not often captured or preserved. In addition, sharing this information amongst health professionals, foster parents, and the minor can be difficult due to the fact that each of these groups of people should only see the information relevant to their role.

Accordingly, the systems and methods described herein provide an integrated health interface system that collects, aggregates, analyzes, and displays health data for one or more users. For example, the integrated health interface system may collect, aggregate, analyze, and display health data for minors that are a part of the foster care system and/or for any other minor or adult patient. The integrated health interface system may aggregate data stored in various databases. For example, one or more of the various entities may be associated with one or more databases that include information related to the healthcare of a patient. The integrated health interface system may retrieve data from these databases, map the data to a set of common terms based on an ontology, and display such information to an entity accessing the system. In one embodiment, instead of converting data received from each of several sources into a standardized format, the integrated health interface system may include a set of ontologies that provide a correlation between fields of data from the various sources and that contain common data types. For example, the integrated health interface system may determine a correlation between a first column header in a first set of fields from a first data source and a second column header in a second set of fields from a second data source using the ontology, store data retrieved from the second data source in a second, local database in association with the second column header, and then may display in a user interface the data associated with the first column header under the second column header (without modifying the actual data).

The health interface system also provides input options so that clinicians, foster parents, guardians, the minor, and/or others can add detail and/or information to the one or more databases.

One aspect of the disclosure provides a computing system configured to access one or more databases in substantially real-time in order to aggregate patient health information and provide the aggregated information to a user in an interactive user interface. The computing system comprises one or more computer processors. The computing system further comprises a plurality of databases each storing respective datasets. The computing system further comprises a second database comprising retrieved datasets organized in a plurality of first fields. The computing system further comprises a computer readable storage medium storing program instructions configured for execution by the one or more computer processor in order to cause the computing system to: for each database in the plurality of databases, access the dataset stored in the respective database, where the accessed dataset comprises data for a plurality of users, and where each data in the retrieved dataset is associated with a second field in a plurality of second fields; identify a name for each second field in the retrieved dataset; determine a mapping between each identified second field name and a name of a first field in the plurality of first fields; and store the accessed dataset in the second database such that each data in the accessed dataset is stored in association with the first field that maps to the second field that the respective data is associated with; receive a request to access the computing system; determine an identity of a user associated with the request to access the computing system; retrieve from the second database user health data that is associated with the determined user; generate a summary of a medical history of the determined user based on the retrieved user health data; and generate user interface data for rendering the interactive user interface on a computing device.

The computing system of the preceding paragraph can have any sub-combination of the following features: where the interactive user interface includes a first container that comprises an identification of at least one first field in the plurality of first fields, where the first container further comprises the retrieved user health data that corresponds with the at least one first field and the generated summary of the medical history of the determined user; where the retrieved user health data comprises medical claims submitted on behalf of the determined user, and where the computer readable storage medium further stores program instructions that cause the computing system to generate the summary of the medical history of the determined user based on the medical claims; where the computer readable storage medium further stores program instructions that cause the computing system to generate an alert associated with the team member based on the retrieved user health data, where the first container comprises the generated alert; where the computer readable storage medium further stores program instructions that cause the computing system to: receive an indication that the generated alert is selected via the interactive user interface, where the generated alert indicates that the user missed an appointment, and update the user interface data such that the interactive user interface includes a second container comprising a list of selectable appointment times that can be reserved for the user; where the computer readable storage medium further stores program instructions that cause the computing system to: receive an indication that the generated alert is selected via the interactive user interface, where the generated alert indicates that the user is missing a lab test, and update the user interface data such that the interactive user interface includes a second container comprising a map that graphically displays a location of one or more lab facilities located near the user where the lab test can be performed; where the retrieved user health data comprises prescription data, where the team member is a primary care physician, and where the alert is generated based on the prescription data; where the computer readable storage medium further stores program instructions that cause the computing system to generate a risk score associated with the user, where the risk score is generated based on the retrieved user health data; where the risk score is generated based on at least one of a number of missing services associated with the user, a priority of each missing service associated with the user, a likelihood that the user seeks medical services without intervention, or a number of times the user does not comply with a recommended care plan; where the mapping between each identified second field name and a name of a first field in the plurality of first fields is determined based on an ontology; where the interactive user interface further includes a second container that comprises a first alert associated with the team member and a second alert associated with the team member, where the first alert corresponds with the user, and where the second alert corresponds with a second user; where the computer readable storage medium further stores program instructions that cause the computing system to: receive text and a selection of a second team member from the team member, and transmit a message to an account associated with the second team member, where the message comprises the text, and where the second team member can view the message when accessing the computing system; where the team member is one of a primary care physician, a pharmacist, a government agency employee, a guardian, or the user.

Another aspect of the disclosure provides a computer-implemented method of accessing one or more databases in substantially real-time in order to aggregate patient health information and provide the aggregated information to a user in an interactive user interface. The computer-implemented method comprises, as implemented by one or more computer systems comprising computer hardware and memory, the one or more computer systems configured with specific executable instructions, retrieving dataset stored in a first database, where the retrieved dataset comprises data for a plurality of users, and where each data in the retrieved dataset is associated with a second field in a plurality of second fields; identifying a name for each second field in the retrieved dataset; determining a mapping between each identified second field name and a name of a first field in a plurality of first fields; storing the retrieved dataset in a second database such that each data in the retrieved dataset is stored in association with the first field that maps to the second field that the respective data is associated with; receiving a request to access the one or more computer systems; determining an identity of a user associated with the request to access the computing system; retrieving from the second database user health data that is associated with the determined user; and generating user interface data for rendering the interactive user interface on a computing device, the interactive user interface including a first container that comprises an identification of at least one first field in the plurality of first fields, where the first container further comprises the retrieved user health data that corresponds with the at least one first field.

The computer-implemented method of the preceding paragraph can have any sub-combination of the following features: where the interactive user interface includes a first container that comprises an identification of at least one first field in the plurality of first fields, where the first container further comprises the retrieved user health data that corresponds with the at least one first field; where the method further comprises generating a summary of a medical history of the determined user based on the retrieved user health data, where the first container further comprises the generated summary of the medical history of the determined user; where the retrieved user health data comprises medical claims submitted on behalf of the determined user, and where the computer-implemented method further comprises generating the summary of the medical history of the determined user based on the medical claim; where the method further comprises generating an alert associated with the team member based on the retrieved user health data, where the first container comprises the generated alert; where the method further comprises receiving an indication that the generated alert is selected via the interactive user interface, where the generated alert indicates that the user missed an appointment, and updating the user interface data such that the interactive user interface includes a second container comprising a list of selectable appointment times that can be reserved for the user; where the method further comprises receiving an indication that the generated alert is selected via the interactive user interface, where the generated alert indicates that the user is missing a lab test, and updating the user interface data such that the interactive user interface includes a second container comprising a map that graphically displays a location of one or more lab facilities located near the user where the lab test can be performed; where the retrieved user health data comprises prescription data, where the team member is a primary care physician, and where the alert is generated based on the prescription data; and where the method further comprises generating a risk score associated with the user, where the risk score is generated based on the retrieved user health data.

BRIEF DESCRIPTION OF THE DRAWINGS

FIG. 3 illustrates a user interface displaying a patient profile.

FIG. 4 illustrates a user interface displaying a patient medical history.

FIG. 5 illustrates a user interface displaying a patient care plan.

FIG. 6 illustrates a user interface displaying a patient health assessment.

FIG. 7 illustrates a user interface displaying a patient clinical evaluation.

FIG. 10 illustrates a user interface displaying a breakdown of claims, visits, and costs by diagnoses and facilities.

DETAILED DESCRIPTION OF SPECIFIC EMBODIMENTS

Overview

Figure 1:
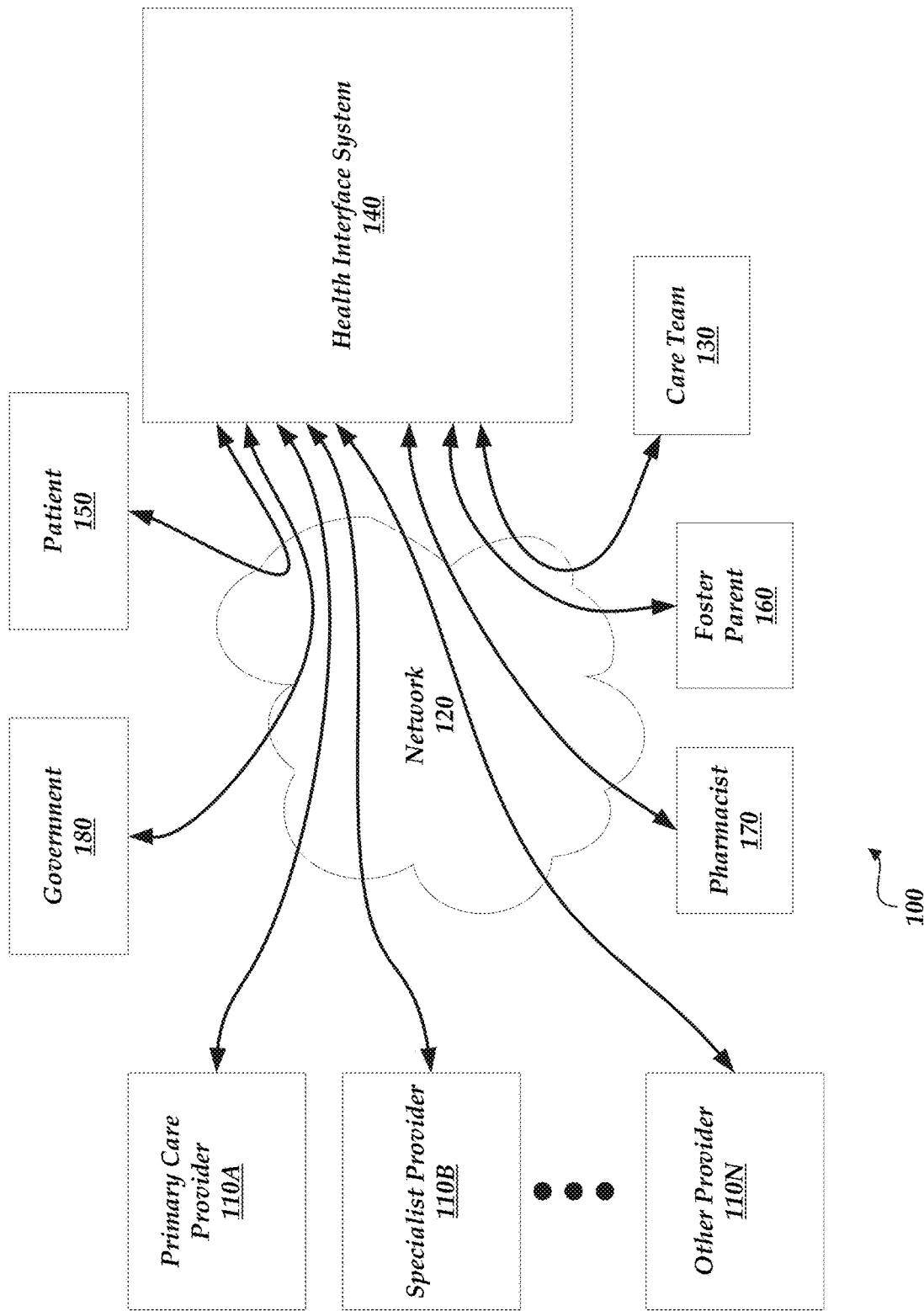
FIG. 1 illustrates a block diagram of a system for aggregating, analyzing, and displaying health data.

As described above, minors in the foster care system may often be placed in multiple foster homes. As a minor transitions from one foster home to another, important information about the minor may be lost. For example, the minor's medical history, hobbies, interests, and/or the like may be lost if the information is not relayed to the guardians of the new foster home. For the medical history in particular, healthcare providers (e.g., physicians, specialists, pharmacists, etc.) often keep detailed records about a patient. However, if the minor transitions from one foster home in a first geographic area to a second foster home in a second geographic area, one or more of the minor's healthcare providers may change. Even if the minor's healthcare records are transferred from an old healthcare provider to a new healthcare provider, such transfers may leave out important information that another healthcare provider knows about the minor. For example, health information related to the minor may be stored in separate databases (e.g., a claims history may be stored in one database, prescription information may be stored in another database, etc.). The separate databases may not be linked or integrated in any way to allow communication of this information among various healthcare providers. Thus, a minor's old pharmacist may be aware of certain medication that the minor is taking, but this information may not be relayed to a new primary care physician.

In some cases, a care team may manage the healthcare of a minor. For example, the care team may include a care team leader and one or more care team members who monitor whether a minor is receiving proper healthcare. The care team may interact with the minor, the minor's guardians, the minor's physician(s), the minor's specialist(s), the minor's pharmacist, and/or government agencies (e.g., state child welfare agencies). However, each of these entities may store different data related to the minor in different, disparate databases, as described above. Thus, the members of the care team may have trouble finding the appropriate health data to ensure that the minor is receiving proper healthcare.

Accordingly, the systems and methods are described herein provide an integrated health interface system that aggregates, analyzes, and displays health data for one or more users. For example, the integrated health interface system may aggregate, analyze, and display health data for minors that are a part of the foster care system. However, this is not meant to be limiting. The integrated health interface system described herein may aggregate, analyze, and display health data for any patient.

The integrated health interface system may be accessible by a plurality of entities. For example, physicians, specialists, pharmacists, patients, guardians, government agencies, and/or the like may access the integrated health interface system. Each of the various entities may be associated with an access level such that a respective entity can only view data that has been authorized for viewing by the respective entity. Alternatively or in addition, the integrated health interface system can support discover permissions where a physician, specialist, pharmacist, patient, guardian, government agencies, and/or another such user can discover that a piece of data is available, but be notified that the respective user does not have permission to view the available data and must gain special permission in order to view the available data.

The integrated health interface system may aggregate data stored in various databases. For example, one or more of the various entities may be associated with one or more databases that include information related to the healthcare of a patient. The integrated health interface system may retrieve data from these databases, map the data to a set of common terms based on an ontology, and display such information to an entity accessing the system. For example, instead of converting the data stored in the databases into a standardized format, the integrated health interface system may include a set of ontologies that provide a correlation between a first set of fields and a second set of fields. The first set of fields may be column headers in a database. The second set of fields may be a list of common column headers that may be included in the displayed information. The integrated health interface system may determine a correlation between a first column header in the first set of fields and a second column header in the second set of fields using the ontology, store data retrieved from the database in a second, local database in association with the second column header, and then may display in a user interface the data associated with the first column header under the second column header (without modifying the actual data). In this way, new databases can be seamlessly linked to the integrated health interface system such that the integrated health interface system can populate a user interface with data from the new database without having to modify the data to fit a standard format.

In an embodiment, the integrated health interface system generates alerts and/or notifications that are associated with specific entities. For example, the alerts and/or notifications may indicate that a task needs to be performed, a task has already been performed, an appointment was missed, lab results are missing, a prescription was not filled or refilled at the proper time, and/or the like. These alerts and/or notifications may be derived from the data stored in the various databases. In addition, an alert and/or notification directed at one entity may be derived from data stored in a database associated with another entity. When logged into the integrated health interface system, an entity (via a device used to log into the integrated health interface system) may also be able to view alerts and/or notifications that are directed to other entities.

In a further embodiment, the integrated health interface system provides actionable services via a generated user interface. For example, the integrated health interface system may generate a user interface that is then rendered by a device operated by an entity when the entity logs into the integrated health interface system. The integrated health interface system can further generate an alert and/or notification to be displayed in the user interface in response to one of the conditions described herein occurring. The alert and/or notification can indicate to a care team member that a patient missed an appointment, that a patient has a missing lab result, and/or the like. In response to a notification that a patient missing an appointment, the user interface may include an option to view available appointment times and schedule a new appointment. As another example, in response to a notification that a patient has a missing lab result, the user interface may include an option to view the locations of nearby facilities that can perform the relevant lab tests and/or to schedule an appointment.

In some embodiments, the alert and/or notification is automatically transmitted to the device operated by the entity associated with the alert and/or notification. The alert and/or notification can be transmitted at the time that the alert and/or notification is generated or at some determined time after generation of the alert and/or notification. When received by the device, the alert and/or notification can cause the device to display the alert and/or notification via the activation of an application on the device (e.g., a browser, a mobile application, etc.). For example, receipt of the alert and/or notification may automatically activate an application on the device, such as a messaging application (e.g., SMS or MMS messaging application), a standalone application (e.g., a health data monitoring application), or a browser, for example, and display information included in the alert and/or notification. If the device is offline when the alert and/or notification is transmitted, the application may be automatically activated when the device is online such that the alert and/or notification is displayed. As another example, receipt of the alert and/or notification may cause a browser to open and be redirected to a login page generated by the integrated health interface system so that the entity can log in to the integrated health interface system and view the alert and/or notification. Alternatively, the alert and/or notification may include a URL of a webpage (or other online information) associated with the alert and/or notification, such that when the device (e.g., a mobile device) receives the alert, a browser (or other application) is automatically activated and the URL included in the alert and/or notification is accessed via the Internet.

Health Interface System Overview

FIG. 1 illustrates a block diagram of a system 100 for aggregating, analyzing, and displaying health data. The system 100 comprises one or more primary care provider devices 110A, one or more specialist provider devices 110G, one or more other provider devices 110N, a care team device 130, a patient device 150, a foster parent device 160, a pharmacist device 170, a government device 180, a health interface system 140, and/or a network 120.

In the embodiment illustrated in FIG. 1, the one or more primary care provider devices 110A (e.g., operated by a doctor, nurse, hospital or clinic staff, etc.), the one or more specialist provider devices 110G (e.g., operated by a specialist, a specialist's staff, etc.), the one or more other provider devices 110N, the care team device 130 (e.g., operated by a care team member or leader), the patient device 150 (e.g., operated by a patient), the foster parent device 160 (e.g., operated by the guardians of a patient), the pharmacist device 170 (e.g., operated by a pharmacist), and the government device 180 (e.g., operated by a member of a government agency, such as a state child welfare agency), which may each be implemented by one or more first physical computing devices, are communicatively connected to the health interface system 140, which may be implemented by one or more second physical computing devices, over the network 120. In some embodiments, each such physical computing device may be implemented as a computer system including some or all of the components illustrated in the example computing system 1500 of FIG. 15. For example, the one or more primary care provider devices 110A, the one or more specialist provider devices 110G, the one or more other provider devices 110N, the care team device 130, the patient device 150, the foster parent device 160, the pharmacist device 170, and the government device 180 may be implemented in a computer system as a set of program instructions recorded on a machine-readable storage medium.

The one or more primary care provider devices 110A, the one or more specialist provider devices 110G, the one or more other provider devices 110N, the care team device 130, the patient device 150, the foster parent device 160, the pharmacist device 170, and the government device 180 may communicate with the health interface system 140 to access health information related to one or more patients. Each of the various entities may be associated with an access level such that a respective entity can only access and view data that has been authorized for viewing by the respective entity. Alternatively or in addition, the health interface system 140 can support discover permissions where an entity can discover that a piece of data is available, but be notified that the respective entity does not have permission to view the available data and must gain special permission in order to view the available data.

One or more of the primary care provider devices 110A, the specialist provider devices 110G, the other provider devices 110N, the care team device 130, the patient device 150, the foster parent device 160, the pharmacist device 170, and the government device 180 may be associated with one or more databases.

For example, the one or more databases may be associated with and/or maintained by various entities. Such entities may include a health maintenance organization (HMO), a social services or other government agency, and/or a data integration system. The HMO database can include medical claims, pharmacy claims, health risk assessments (e.g., GAIN-SS, PCS-17, etc.), electronic medical records, lab results, vitals (e.g., blood pressure, heart rate, etc.), care plan data (e.g., a patients' primary care and/or treating physicians, current medications, allergies, and/or other clinically relevant information), immunization records, prior authorization information, case management system data, and/or the like. The government agency database can include details about patients' foster parents, guardians, and/or primary care givers, criminal records, school records, and/or the like. The data integration system database can include enriched metrics (e.g., metrics derived from combining data stored in one or more databases). Enriched metrics can include average medical expenditure per month, average pharmacy expenditure per month, average total expenditure (e.g., medical and pharmacy) per month, predicted medical, pharmacy, and/or total expenditure per month, a patient's deviation from expected costs per month, a number of unique prescribers, a number of unique medications (used by one patient or patients in the aggregate), a number of Schedule 2 drugs (as defined by the United States Controlled Substances Act) used by one patient or patients in the aggregate, a costliest diagnosis, an average emergency room utilization rate, an average primary care physician visit rate, a distance to an assigned primary care physician for one or more patients, an average in-patient rate, geo-spatial data about patients, care teams, and/or health facilities, health risk scores, a number of missing medical services for which patients are eligible, and/or the like.

The one or more of the primary care provider devices 110A, the specialist provider devices 110B, the other provider devices 110N, the care team device 130, the patient device 150, the foster parent device 160, the pharmacist device 170, and/or the government device 180 may receive data from the one or more databases via an application programming interface (API) or adaptor, a connection interface, and/or other access point to a transactional or data warehouse system maintained by the HMO and/or government agency. Data can also be stored at a central location (e.g., a server) and delivered to the various entities via a network. Data can also be stored locally on a storage medium (e.g., a hard disk, optical disk, solid state drive, memory, etc.).

The health interface system 140 may aggregate data stored in the various databases. For example, the health interface system 140 may retrieve data from these databases, map the data to a set of common terms based on an ontology, and generate one or more user interfaces to display such information to an entity accessing the health interface system 140, as described in greater detail below. Rather than converting the data stored in the databases into a standardized format, the health interface system 140 may include a set of ontologies that provide a correlation between a first set of fields and a second set of fields. For example, the first set of fields may be column headers in a database and the second set of fields may be a list of common column headers that may be included in the generated user interface. The health interface system 140 may determine a correlation between a first field in the first set of fields and a second field in the second set of fields using the ontology, store data retrieved from the database in a second, local database (e.g., local to the health interface system 140) in association with the second field, and then may display in a user interface the data associated with the first field under the second field (without modifying the actual data). In this way, new databases can be seamlessly linked to the health interface system 140 such that the health interface system 140 can populate a user interface with data from the new database without having to modify the data to fit a standard format.

When executed by one or more processors of the computer system, logic in the health interface system 140 is operable to aggregate, analyze, and display health data according to the techniques described herein. In one embodiment, the health interface system 140 may be implemented in a Java Virtual Machine (JVM) that is executing in a distributed or non-distributed computer system. In other embodiments, the health interface system 140 may be implemented as a combination of programming instructions written in any programming language (e.g. C++ or Visual Basic) and hardware components (e.g., memory, CPU time) that have been allocated for executing the program instructions.

In an embodiment, the network 120 includes any communications network, such as the Internet. The network 120 may be a wired network, a wireless network, or a combination of the two. For example, network 120 may be a local area network (LAN) and/or a wireless area network (WAN).

Example User Interfaces

Figure 2:
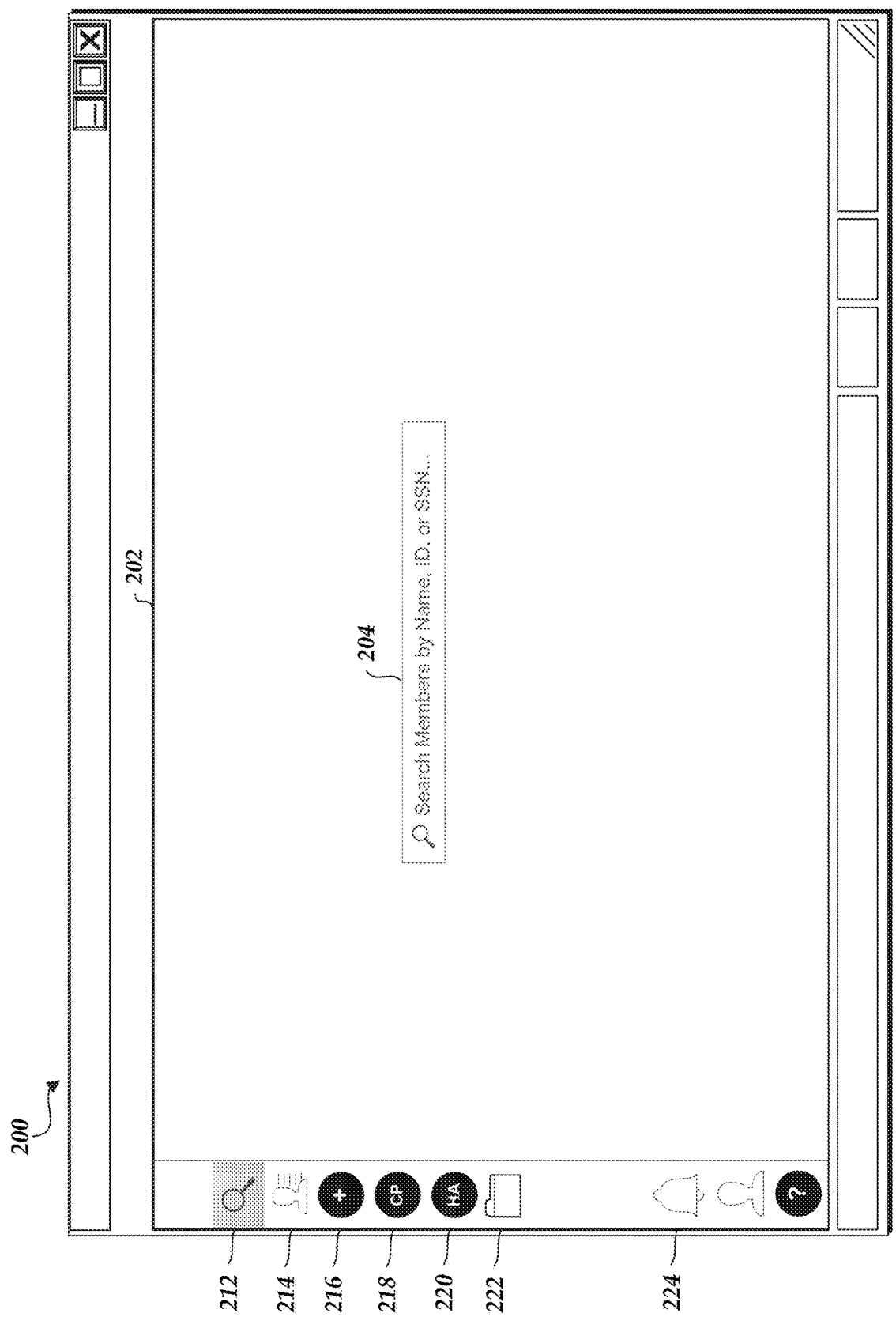
FIG. 2 illustrates a user interface displaying an ability to search for patients.

FIG. 2 illustrates a user interface 200 displaying an ability to search for patients. The interface 200 may be generated by the health interface system 140 and viewable on any of the entities in communication with the health interface system 140. As illustrated in FIG. 2, the interface 200 includes a pane 202. The pane 202 may display data according to a button selected by the user. For example, the user may have selected search button 212. Thus, the pane 202 may include a search box 204 that allows a user to search for a patient. The user may search for a patient by providing the patient's name, identification, social security number, or any other unique identifier. Searching for a patient may bring up information about the patient, such as the patient's profile, which is described below with respect to FIG. 3.

FIG. 3 illustrates a user interface 300 displaying a patient profile. The interface 300 may be generated by the health interface system 140 and viewable on any of the entities in communication with the health interface system 140. As illustrated in FIG. 3, the user has selected profile button 214. Thus, the pane 202 may include various data derived from the linked databases, such as biographical data about the patient, the hobbies and/or interests of the patient, some fun facts about the patient, and/or health data associated with the patient. Some of the data may be retrieved directly from a database and displayed in the pane 202 (after the ontology is used to determine a correlation or mapping between database fields and common fields).

Other data may be generated and displayed based on an analysis of the data retrieved from one or more databases. For example, information displayed in the medical snapshot section may be derived from medical and/or pharmaceutical claims data. Medical claims may include claims that are submitted to insurance companies to receive payment for medical services administered by the healthcare provider. Likewise, pharmaceutical claims may include claims that are submitted to insurance companies to receive payment for drugs distributed by the healthcare provider. Similarly, information related to the most seen primary care provider (PCP) or the last seen specialist in the contacts section may be derived from the medical and/or pharmaceutical claims.

As another example, information displayed in the medical snapshot section may include a map that shows the location of a patient relative to a location of one or more providers and/or health facilities involved in the care of the patient, an average distance traveled by a patient to receive care (e.g., to measure health access friction), a current deviation of a patient's expected or predicted costs, a current deviation from expected costs as a number of standard deviations from a population average, a propensity score predicting the likelihood that a patient's medical costs may deviate by a threshold value in the future, one or more top medical conditions that contribute the most to patient costs (e.g., from aggregated medical claims data), suspected conditions (e.g., conditions suspected to be suffered by a patient based on a mapping of diagnosis codes to conditions assigned to and/or associated with the patient), a number of missing services for which a patient is eligible (e.g., if asthmatic, a determination can be made whether the patient has received a prescription for a preventer medication in the calendar year), a sum of possibly preventable emergency room expenditures (e.g., for emergency room admissions, diagnoses can be assigned a probability that that condition could have been treated in an alternative facility or avoided. The sum of the probability multiplied by the actual treatment expenditure can provide a possibly preventable expenditure value), and/or the like.

In an embodiment, a user can generate a report that includes some or all of the displayed health data in the pane 202 by selecting report button 302. The generated report may be made available to other entities that access the health interface system 140 (e.g., accessible when the other entities log in to the health interface system 140).

The user interface 300 may also provide actionable services. As described above, the health interface system 140 can generate alerts and/or notifications to be displayed in the user interface 300 in response to a determination that a task needs to be performed, a task has already been performed, an appointment was missed, lab results are missing, a prescription was not filled or refilled at the proper time, and/or the like. The generated alerts and/or notifications can be displayed in the user interface 300. For example, the notifications/alerts section in the user interface 300 indicates that the patient missed a service. Other actionable services that can be depicted in the user interface 300 include allowing a user to schedule an appointment if a notification indicates that an appointment was missed, assigning a patient to a specific health intervention (e.g., health coaching) so as to tag the patient and transmit the patient's information to a team for outreach, sending a secure message to any individual of the patient's care team, re-assigning the patient's PCP to another provider (e.g., someone closer to the patient, a provided experienced in the particular condition(s) of the patient, etc.), exporting a summary and/or full report of the patient's medical history (including all patient information) for the purposes of facilitating a hand-off to another provider, sending a reminder for an appointment and/or prescription collection to the patient or a person associated with the patient (e.g., the patient's foster parent, parent, guardian, care giver, etc.), issuing a new patient ID card to a patient if the patient lost one, re-assigning a patient to a new case manager or any other health care provider, and/or the like. Accordingly, the user may select the notification or otherwise indicate that the user would like to schedule an appointment for the patient so that the patient receives the service. In response to a selection of the notification or an indication that the user would like to schedule an appointment, the user interface 300 may display a list of available appointment times to see the relevant provider. In addition, the user interface 300 may display a map to show the geographic location of one or more providers so that the user can choose, for example, the provider nearest to the patient.

In some embodiments, the alert and/or notification is automatically transmitted to an entity in communication with the health interface system 140. The alert and/or notification can be transmitted by the health interface system 140 at the time that the alert and/or notification is generated or at some determined time after generation of the alert and/or notification. When received by the entity, the alert and/or notification can cause the entity to display the alert and/or notification via the activation of an application on the entity (e.g., a browser, a mobile application, etc.). For example, receipt of the alert and/or notification may cause a mobile application to generate a push notification that is displayed. As another example, receipt of the alert and/or notification may cause a browser to open and be redirected to a login page generated by the health interface system 140 so that the entity can log in to the health interface system 140 and view the alert and/or notification via the user interface 300.

FIG. 4 illustrates a user interface 400 displaying a patient medical history. The interface 400 may be generated by the health interface system 140 and viewable on any of the entities in communication with the health interface system 140. As illustrated in FIG. 4, the user has selected medical history button 216. Thus, the pane 202 may include various data derived from the linked databases related to the medical history of the patient, such as past lab results, medications taken by the patient, allergies of the patient, the last visits to see a provider by the patient, and/or the like. For example, the medications data may be derived from the database that stores pharmaceutical claims.

The pane 202 may further include a risk score in the medical profile section. The risk score may represent a propensity for observed medical costs associated with a patient to deviate significantly (e.g., more than a threshold value) from expected medical costs within a time period (e.g., 12 months). The risk score may be based on claims data (e.g., medical and pharmaceutical claims data), coverage data (e.g., patient coverage/eligibility information), patient demographic data, a number of missing services associated with the patient, a priority of each missing service associated with the patient, a likelihood that the patient seeks medical services without intervention, a number of times the patient does not comply with a recommended care plan, a sum of amounts paid on medical claims for a patient (e.g., over a period of time, such as 12 months), an average amount paid on medical claims for a patient (e.g., over a period of time, such as 12 months), a per patient per month medical cost (e.g., over a period of time, such as 12 months), a sum of amounts paid on pharmaceutical claims for a patient (e.g., over a period of time, such as 12 months), an average amount paid on pharmaceutical claims for a patient (e.g., over a period of time, such as 12 months), a per patient per month pharmaceutical cost (e.g., over a period of time, such as 12 months), a per patient per month combined medical and pharmaceutical cost (e.g., over a period of time, such as 12 months), a sum of amounts paid on medical and pharmaceutical claims for a patient (e.g., over a period of time, such as 12 months), a difference between expected cost (e.g., a capitation rate given a set of Hierarchical Condition Categories (HCCs) adjusted for medical loss ratio) and observed cost (e.g., over a period of time, such as 12 months), a population average difference between expected cost and observed cost (e.g., over a period of time, such as 12 months), a population standard deviation of difference between expected cost and observed cost (e.g., over a period of time, such as 12 months), a per-patient deviation from expected costs (e.g., in standard deviations) from the population average (e.g., over a period of time, such as 12 months), a sum of a patient's HCC coefficients (e.g., over a period of time, such as 12 months), a capitation rate given a set of HCCs and a Centers for Medicare and Medicaid Services (CMS) plan rating of at least three and a half stars (e.g., over a period of time, such as 12 months), a capitation rate given a set of HCCs adjusted for medical loss ratio (e.g., over a period of time, such as 12 months), a sum of emergency room encounters (e.g., over a period of time, such as 12 months), a sum of possibly preventable emergency room costs (e.g., over a period of time, such as 12 months), a sum of in-patient encounters (e.g., over a period of time, such as 12 months), a list of unique national drug code (NDC) codes for drugs prescribed (e.g., over a period of time, such as 12 months), a list of unique drug names for drugs prescribed (e.g., over a period of time, such as 12 months), a list of unique pharmacological classes for drugs prescribed (e.g., over a period of time, such as 12 months), a list of unique Drug Enforcement Agency (DEA) Schedules for drugs prescribed (e.g., over a period of time, such as 12 months), a count of unique drugs prescribed (e.g., over a period of time, such as 12 months), flags for different condition categories based on a proprietary mapping of ICD-9, CPT, and HCPCS codes to suspected conditions (e.g., over a period of time, such as 12 months), flags for different HCCs based on CMS mapping of ICD-9 codes to chronic conditions (e.g., over a period of time, such as 12 months), and/or the like. For example, the expected medical costs may be a cost that would be expected given a patient's disease burden and calculated by assigning HCCs to members, summing the capitation premium for those HCCs, and adjusting for medical loss ratio. Observed medical costs can be calculated as per patient per medical costs over eligible months during the relevant time period. The deviation from expected medical costs is then calculated by subtracting observed medical costs from expected medical costs.

The risk factors may be weighted to generate the risk score. For example, some patients may have experienced an acute incident in their recent past that has caused their cost and utilization to spike temporarily. The medical costs associated with these patients may regress to the cost and/or utilization mean and may not benefit significantly from care management resources (as the chronically ill or poorly managed patients would). To address the possibility of regressing to the cost and/or utilization mean, the health interface system 140 can categorize a patient into one of three groups: high-deviation (e.g., observed average monthly medical costs exceed expected average monthly medical costs by a threshold value), chronic (e.g., a patient that has one or more high risk chronic conditions, as suggested by the patient's claim history, but whose observed average monthly medical costs do not exceed expected average monthly medical costs by the threshold value), or non-chronic low-deviation (e.g., a patient that does not have one or more high risk chronic conditions, as suggested by the patient's claim history, and whose observed average monthly medical costs do not exceed the expected average monthly medical costs by the threshold value). Once categorized, the health interface system 140 can train nine different logistic regression models, one for each of the following state transitions: high-deviation to high-deviation, high-deviation to chronic, high-deviation to non-chronic low-deviation, chronic to high-deviation, chronic to chronic, chronic to non-chronic low-deviation, non-chronic low-deviation to high-deviation, non-chronic low-deviation to chronic, and non-chronic low-deviation to non-chronic low-deviation. The training set for each model may include a sample of all eligible patients. The model training can use L1 regularization to address the collinearity between several of the cost metrics by inducing sparseness on the model. For each patient, the health interface system 140 can generate features for a period of time (e.g., 12 months) before and a period of time (e.g., 12 months) after a selected split date. The output of each model training cycle can be a set of feature weights (e.g., coefficients in a logistic regression model) that can be used to compute propensity scores for each of the state transitions listed above.

Once trained, the health interface system 140 can calculate propensity scores (e.g., a likelihood that a patient will move in to or remain in a given state for a period of time, such as 12 months) for a patient for each of the patient's three possible state transitions (e.g., there are three possible state transitions because the patient has already been categorized as starting in one of three categories). For each state transition, features can be weighted according to a trained model. The health interface system 140 can rank some or all patients by a propensity score associated with the transition to a high-deviation state, and the ranking of a patient can be translated into a risk score. In some embodiments, the user interface 400 may provide the option to the user to customize the weighting employed to generate the risk score (e.g., the factors used to generate the risk score, the threshold value that determines whether a patient is categorized as high-deviation, etc.).

The user may select care plan button 402 to view a patient's care plan, as described below with respect to FIG. 5, and the user may select health assessment button 404 to view a patient's health assessment, as described below with respect to FIG. 6.

FIG. 5 illustrates a user interface 500 displaying a patient care plan 502. The interface 500 may be generated by the health interface system 140 and viewable on any of the entities in communication with the health interface system 140. As illustrated in FIG. 5, the user has selected care plan button 218. Thus, the pane 202 displays the care plan 502. The care plan 502 may allow all authorized members of the care team to view the current and past care plans for the patient. Centralized storage of this data via the health interface system 140 may allow care team members and patient's providers access to baseline data in order to gauge the effectiveness and/or progress that a patient has made in any given care plan. The availability of care plans may also allow some or all of the various entities the ability to collaborate on current care plan goals and/or monitor progress.

In some embodiments, the care plan 502 is interactive. For example, the health interface system 140 can receive the care plan via an API such that one or more fields are editable (by an entity with sufficient permissions) when displayed in the user interface 500. The user interface 500 can display relevant input options showing the editable fields when an editable field is selected. If a field is edited, the health interface system 140 can synch the updated care plan 502 with the health plan's case management system. In other embodiments, the care plan 502 is static (e.g., received as a PDF)

FIG. 6 illustrates a user interface 600 displaying a patient health assessment. The interface 600 may be generated by the health interface system 140 and viewable on any of the entities in communication with the health interface system 140. As illustrated in FIG. 6, the user has selected health assessment button 220. Thus, the pane 202 displays a patient health assessment. The health assessment may allow all authorized members of the care team to view the current and/or past health assessments that have been conducted for the patient. The availability of these assessments may enable some or all members of the care team to access information that is critical in addressing each patient's specific needs. In addition to allowing a historical starting measure of the patient, assessment information may also allow the care team to determine when new assessments should be generated.

FIG. 7 illustrates a user interface 700 displaying a patient clinical evaluation. The interface 700 may be generated by the health interface system 140 and viewable on any of the entities in communication with the health interface system 140. As illustrated in FIG. 7, the user has selected vitals button 222. Thus, the pane 202 displays a set of clinical evaluations for the patient. The clinical evaluations may include date-specific recorded vitals signs, such as temperature, pulse, blood pressure, and/or respiratory rate. These vitals may allow providers to view a summary of the patient's health vitals and determine whether it is necessary to determine changes in a health status observed by different providers. Each instance of vitals may allow entities to enter notes regarding dated entries and observations.

Figure 8:
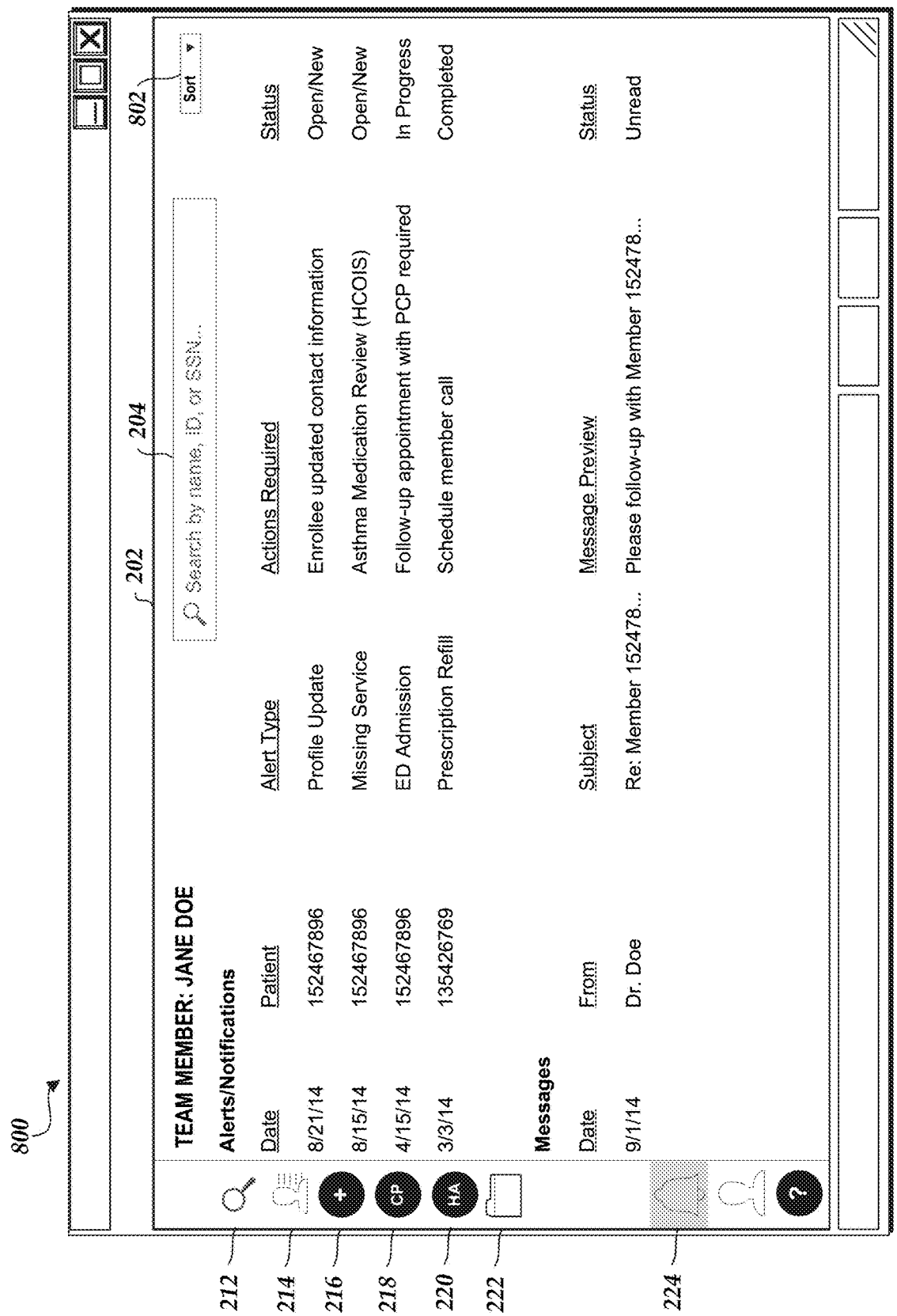
FIG. 8 illustrates a user interface displaying alerts and messages for a care team member.

FIG. 8 illustrates a user interface 800 displaying alerts and messages for a care team member. The interface 800 may be generated by the health interface system 140 and viewable on any of the entities in communication with the health interface system 140. As illustrated in FIG. 8, the user has selected alert button 224. Thus, the pane 202 displays alerts and/or notifications. The alerts and/or notifications may be for one or more patients that the viewing entity provides services for. The alerts and/or notifications may be derived from data stored in the databases. Example alerts and/or notifications can include a close appointment alert (e.g., a patient has an appointment coming up in the next week, day, hour, etc.), a missed appointment alert (e.g., if a patient missing an appointment), a propensity score shift (e.g., if a patients' propensity or risk score status changes, and the health provider can also be alerted), a recent admission to an emergency room (or a pre-authorization request from a health provider), a recent in-patient event (or pre-authorization request from a health provider), no interaction by the patient with the health interface system 140 for a period of time (e.g., 6 months), reminders for scheduled check-ins with a patient, and/or the like, In some cases, the alerts and/or notifications may be generated based on data associated with an entity that is different than the entity that has logged into the health interface system 140. For example, a pharmacist may have logged into the health interface system 140 and an alert may have been generated for the pharmacist based on data stored in a database associated with a primary care provider.

The notifications may inform an entity of what tasks have been accomplished and what tasks still need to be accomplished. The notifications and/or alerts may be color-coded to indicate an entity associated with the notification and/or alert and/or to indicate an importance of the notification and/or alert (e.g., green may mean the notification and/or alert is not vital, whereas red may mean the notification and/or alert is urgent).

In an embodiment, entities can communicate with each other via the health interface system 140. For example, one entity can send a message to another entity via the health interface system 140. Any messages sent via the health interface system 140 may be viewable in the user interface 800 in the messages section.

Example User Interfaces Depicting Additional Analytics

Figure 9:
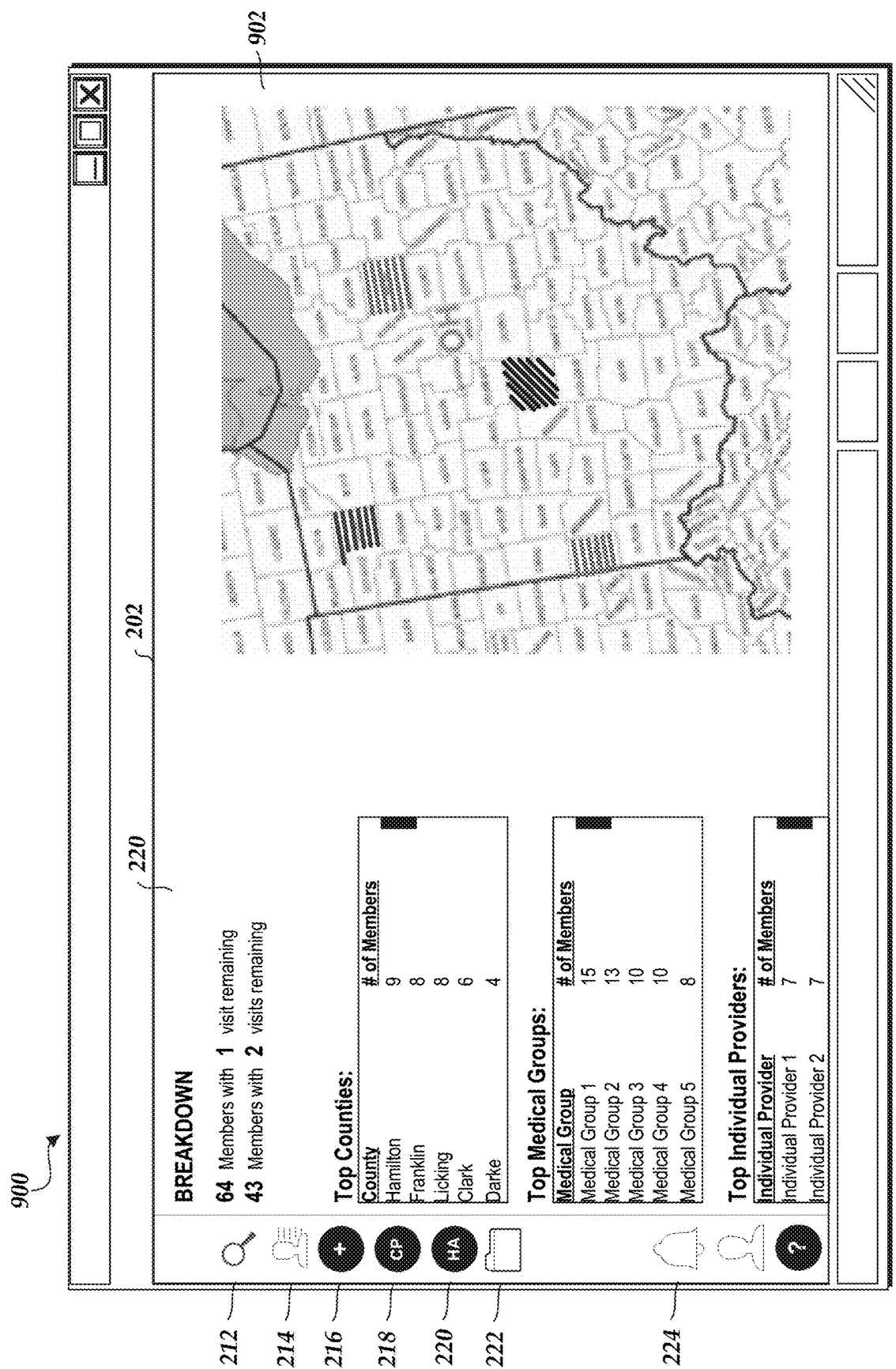
FIG. 9 illustrates a user interface displaying a breakdown of remaining member visits by county.

In some cases, the health interface system 140 can analyze health data at a macro level to, for example, provide insight on the features of a patient population as a whole in a given geographic region. FIG. 9 illustrates a user interface 900 displaying a breakdown of remaining member visits by county. The interface 900 may be generated by the health interface system 140 and viewable on any of the entities in communication with the health interface system 140. As illustrated in FIG. 9, a map 902 indicates a location, by county, of patients that may require a visit (e.g., a well-child visit) within a given period of time (e.g., 90 days). The map 902 may include shading to indicate counties that have a high number of required visits and a low number of required visits. The pane 202 may include a numerical breakdown of the number of required visits by county, medical group, and/or provider.

FIG. 10 illustrates a user interface 1000 displaying a breakdown of claims, visits, and costs by diagnoses and facilities. The interface 1000 may be generated by the health interface system 140 and viewable on any of the entities in communication with the health interface system 140. As illustrated in FIG. 10, the pane 202 includes a list of the top diagnoses by cost associated with emergency room visits for a given patient population.

Figure 11:
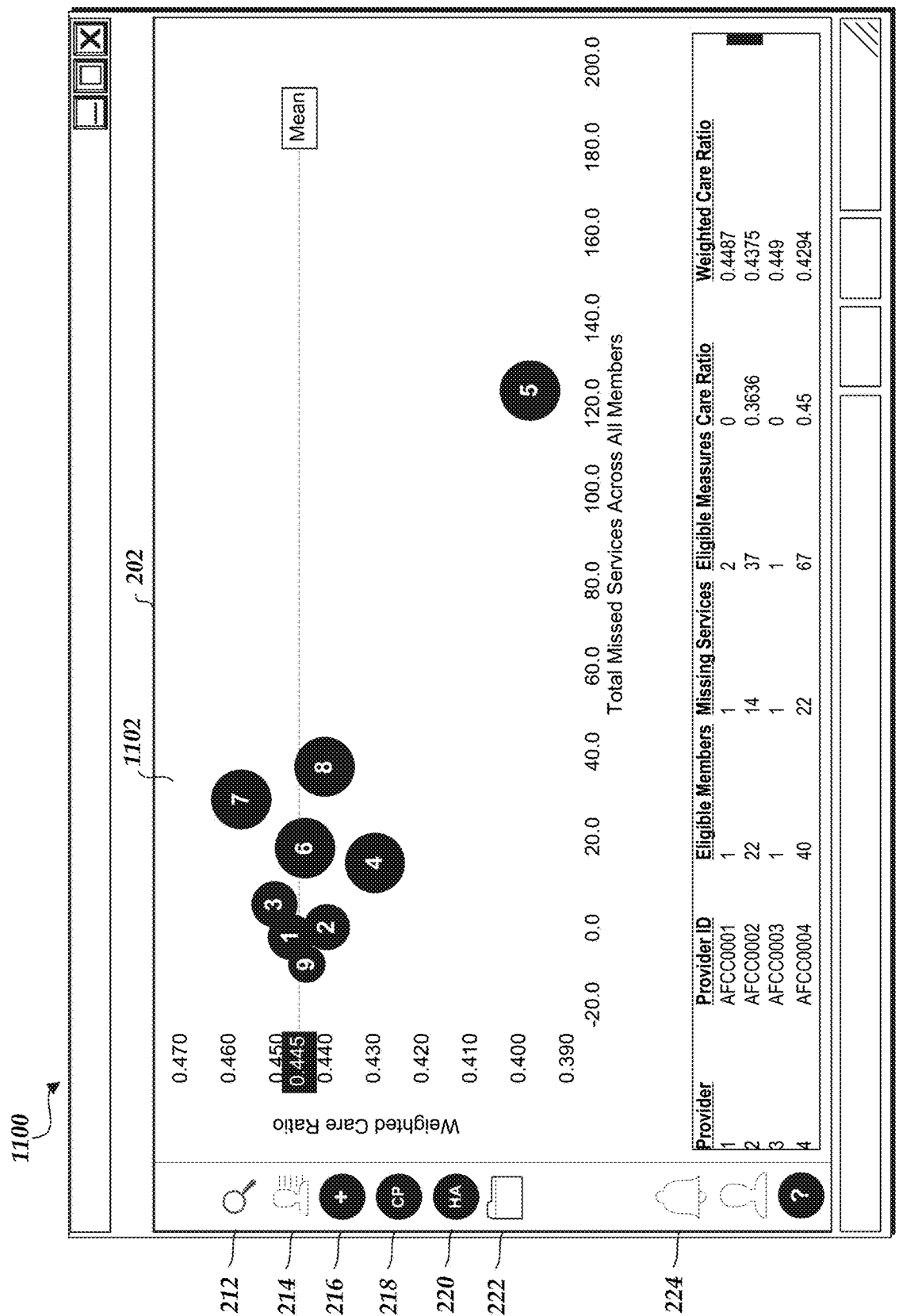
FIG. 11 illustrates a user interface displaying a graph of weighted care ratio by healthcare provider.

FIG. 11 illustrates a user interface 1100 displaying a graph 1102 of weighted care ratio by healthcare provider. The interface 1100 may be generated by the health interface system 140 and viewable on any of the entities in communication with the health interface system 140. As illustrated in FIG. 11, the pane 202 includes the graph 1102 and a table that display a provider network as assessed by their care ratio (e.g., the percentage of associated patients who actually received the medical services for which they were eligible), which can be determined by the health interface system 140. The care ratio and the weighted care ratio allow entities to evaluate the character of the provider network when it comes to identifying which providers are best suited to caring for a patient in the patient population.

In an embodiment, a care ratio is a measure of compliance, applicable to providers, and can be specific to a particular medical service. A care ratio can be a percentage of how many patients eligible for a particular service have actually received that service. For example, if a provider has 100 diabetics associated with them, and there is an interest in knowing how many of these diabetics have had an HbA1c test in the last 12 months, the health interface system 140 would take the number of diabetics receiving this test and divide that by the total number of eligible patients. If the number of diabetics receiving this test is 60 and the total number of eligible patients is 100, the provider's care ratio would therefore be 60%.

In an embodiment, a weighted care ratio is a measure of how well a provider is addressing a particular missing service for their assigned patients for the purposes of comparing providers. The weighted care ratio is weighted because the ratio takes into account the number of patients that are assigned to a provider. The care ratios of providers with more patients may contribute proportionally more to the population average for all providers. Providers with very few patients may typically be assigned the average for the population rather than their true care ratio. The weighted care ratio can avoid overemphasizing the care ratio of a provider that has just a few patients. For example, if the care ratio is "percent of membership receiving an HbA1c test in last 12 months" (e.g., a measure applicable to diabetics only), and a provider only has one patient with diabetes and that patient has not had that service, then that provider's care ratio would be 0%. Instead, applying the logic of the weighted care ratio, that provider would receive the average care ratio for the population (e.g., 60%). Thus, this can prevent over-indexing on providers assigned to small populations of patients.

Example User Interfaces Depicting Actionable Services

Figure 12A:
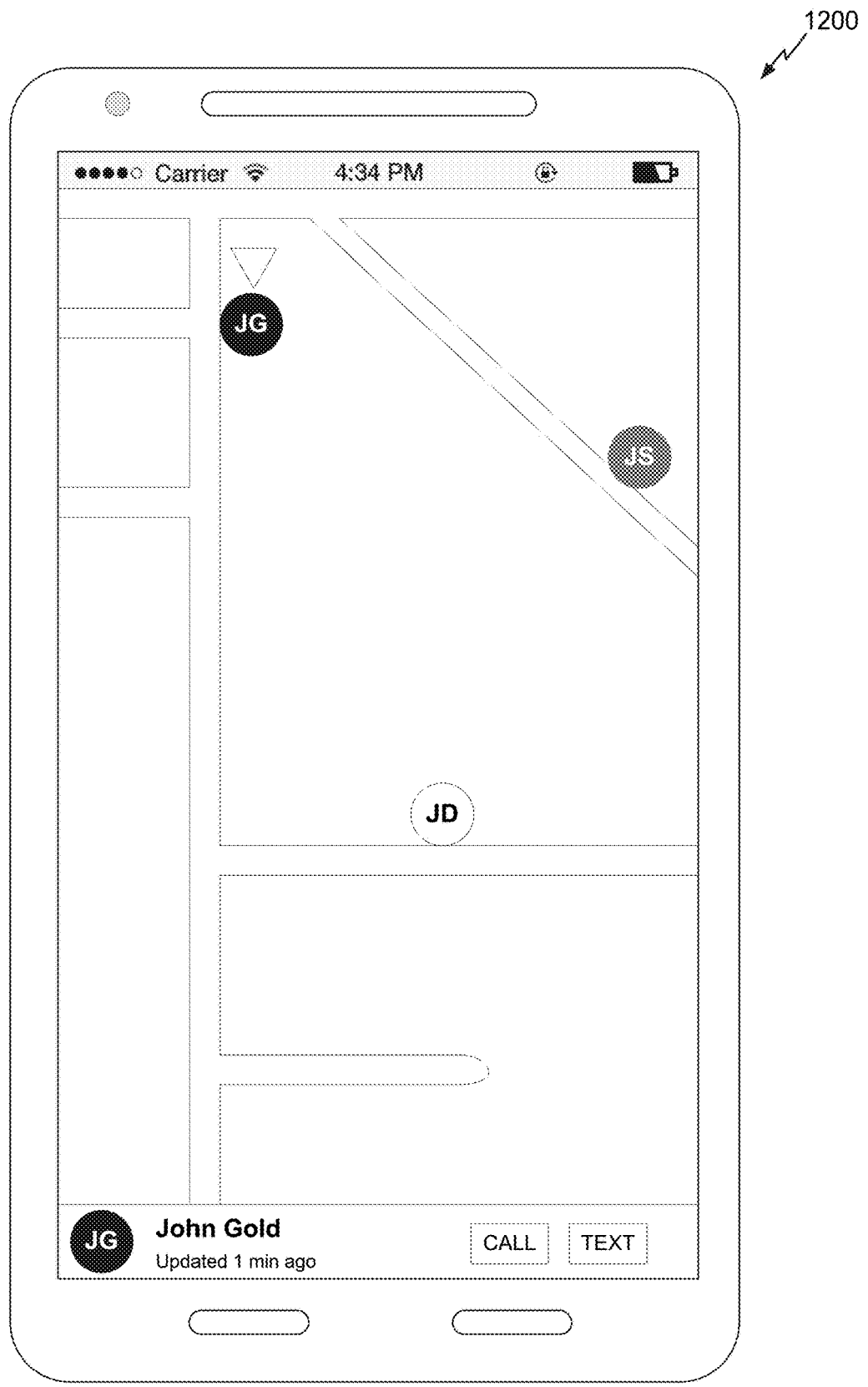
FIGS. 12A-12B illustrate user interfaces displaying a location of care team members.
Figure 12B:
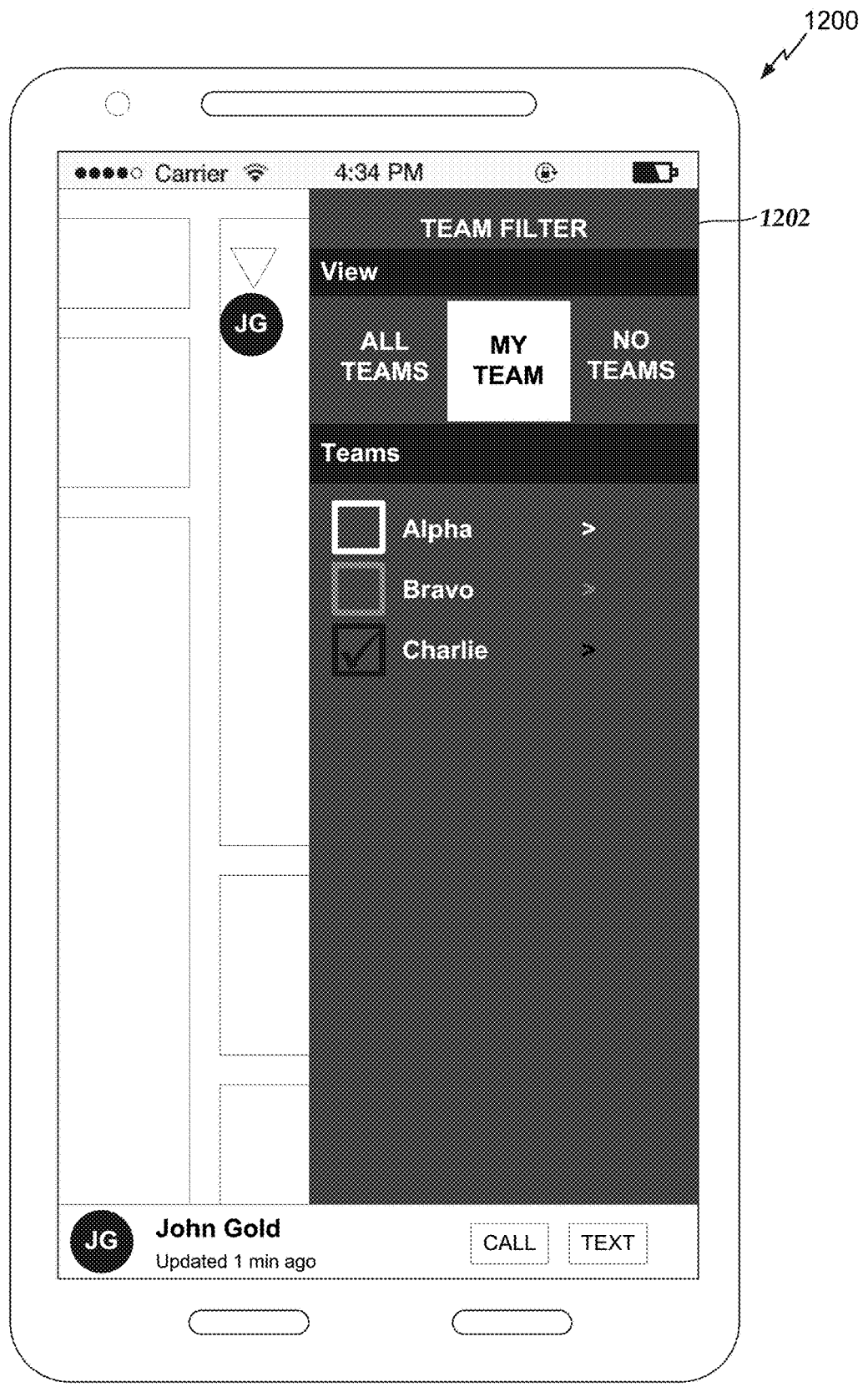

FIGS. 12A-12B illustrate user interfaces 1200 displaying a location of care team members. The interface 1200 may be generated by the health interface system 140 and viewable on any of the entities in communication with the health interface system 140. As illustrated in FIG. 12A, the location of various care team members in one or more care teams is displayed. For example, the care team members may be shaded to indicate what team the care team member is a member of. The interface 1200 may also an entity to contact a care team member that is selected. For example, care team member John Gold is selected and thus may be contacted via phone or electronic message (e.g., text message).

As illustrated in FIG. 12B, a filter 1202 can be selected such that one or more care team members can be hidden. For example, the entity may select one or more care teams, and those care team members that are not a member of the selected care team may disappear from the interface 1200.

Figure 13:
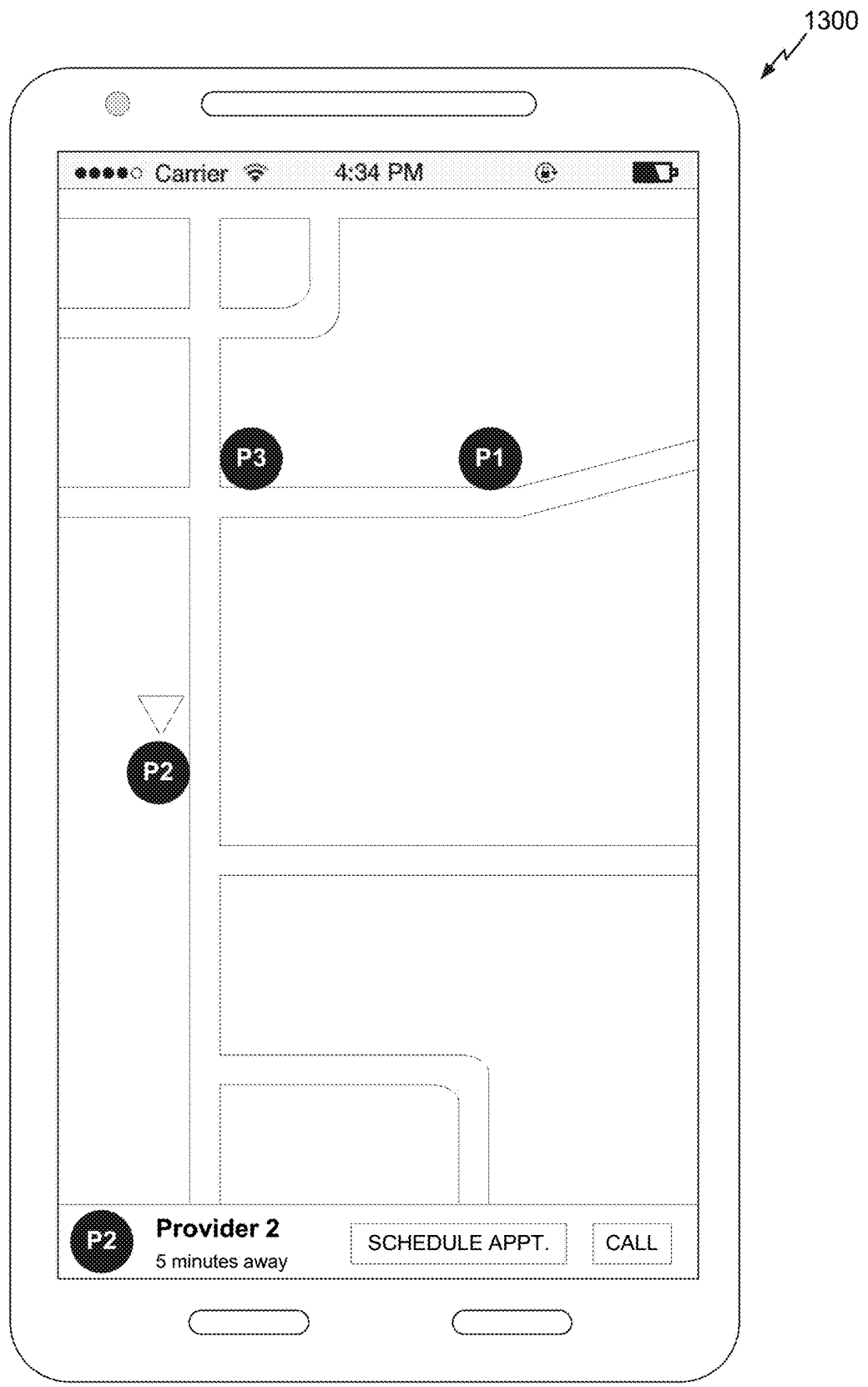
FIG. 13 illustrates a user interface displaying a location of healthcare providers.

FIG. 13 illustrates a user interface 1300 displaying a location of healthcare providers. The interface 1300 may be generated by the health interface system 140 and viewable on any of the entities in communication with the health interface system 140. As illustrated in FIG. 13, the location of various providers is displayed. For example, the providers nearest to a patient may be displayed. The interface 1300 may also an entity to contact a provider that is selected and/or to schedule an appointment with a selected provider. For example, provider 2 is selected. An entity may contact provider 2 via the phone or may be redirected to a page that allows the entity to schedule an appointment with the provider.

Example Process Flow

Figure 14:
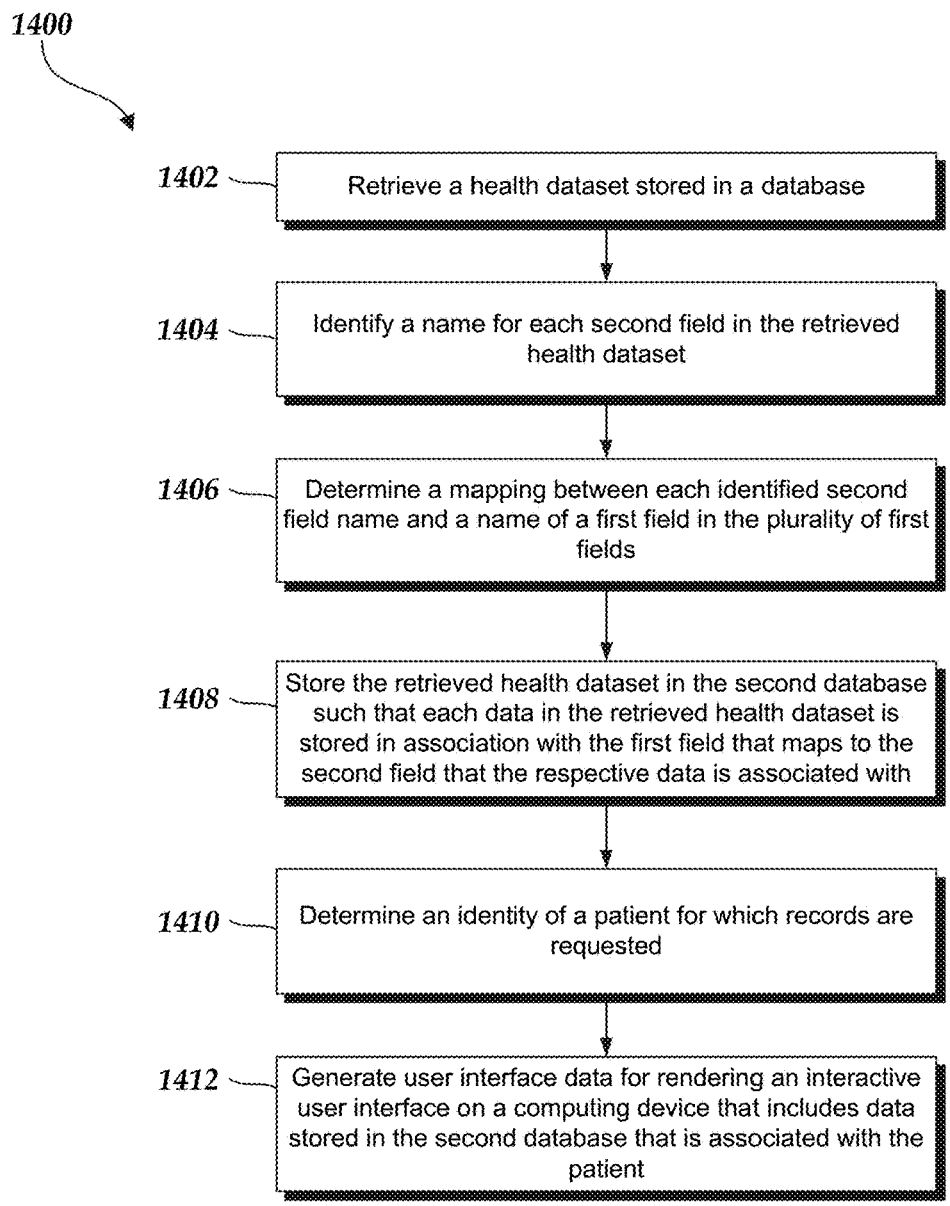
FIG. 14 is a flowchart depicting an illustrative operation of aggregating, analyzing, and displaying health data.

FIG. 14 is a flowchart 1400 depicting an illustrative operation of aggregating, analyzing, and displaying health data. Depending on the embodiment, the method of FIG. 14 may be performed by various computing devices, such as by the health interface system 140. Depending on the embodiment, the method of FIG. 14 may include fewer and/or additional blocks and the blocks may be performed in an order different than illustrated.

In block 1402, a health dataset stored in a database is retrieved. For example, the health dataset may include medical and/or pharmaceutical claims data. The health dataset may include a set of second fields (e.g., columns).

In block 1404, a name for each second field in the retrieved health dataset is identified. In block 1406, a mapping between each identified second field name and a name of a first field in a plurality of first fields is determined. The plurality of first fields may include common terms.

In block 1408, the retrieved health dataset is stored in a second database such that each data in the retrieved health dataset is stored in associated with the first field that maps to the second field that the respective data is associated with. For example, the data may be unchanged, however the column headers for the data may be modified.

In block 1410, an identity of a patient for which records are requested is determined. For example, a care team member may desire to view the records of a specific patient.

In block 1412, user interface data is generated for rendering an interactive user interface on a computing device that includes data stored in the second database that is associated with the patient. The interactive user interface may display an identification of the first fields in association with the data.

Implementation Mechanisms

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 15:
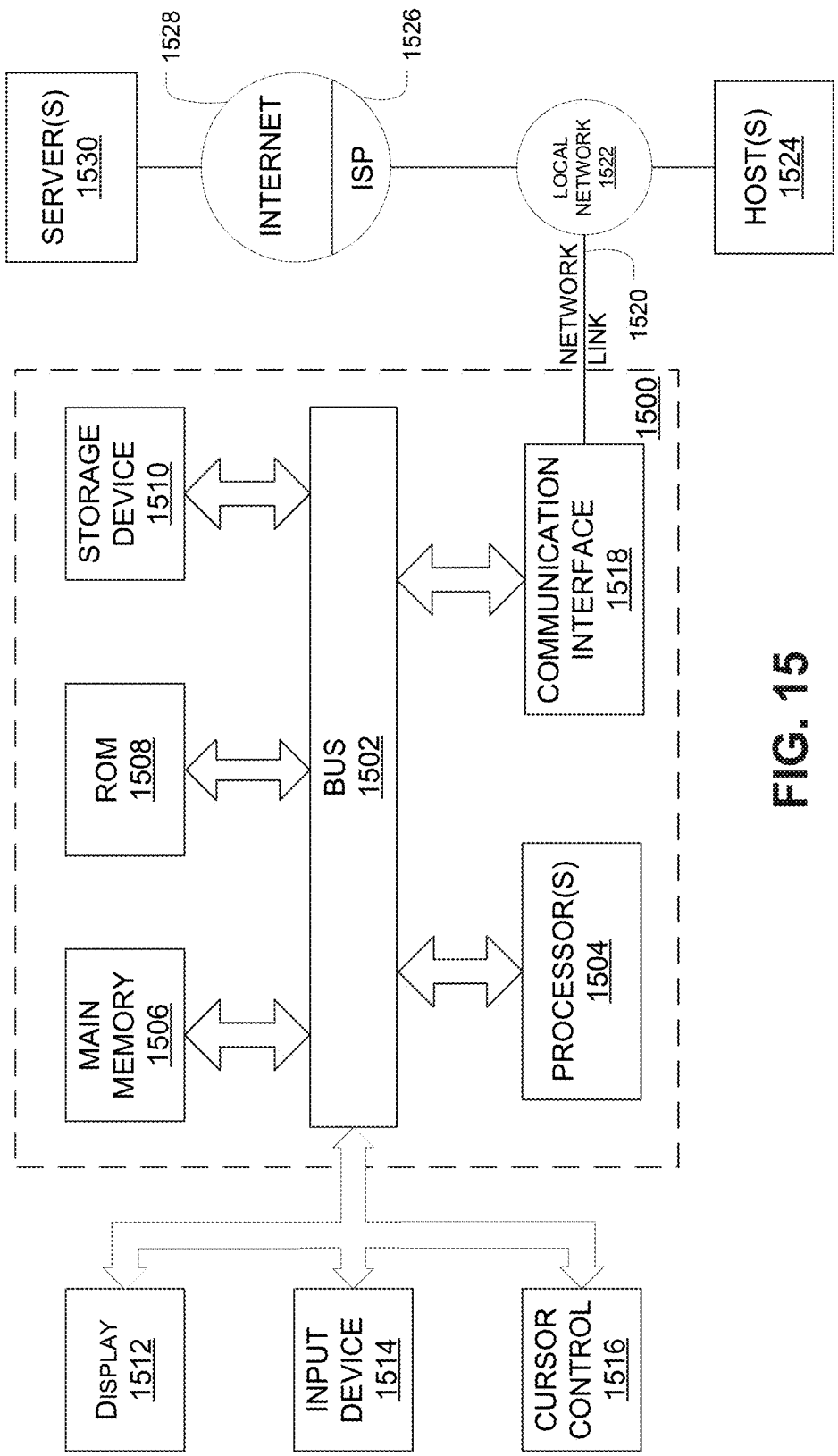
FIG. 15 illustrates a computer system with which certain methods discussed herein may be implemented.

For example, FIG. 15 is a block diagram that illustrates a computer system 1500 upon which an embodiment may be implemented. For example, any of the computing devices discussed herein, such as the one or more primary care provider devices 110A, the one or more specialist provider devices 110B, the one or more other provider devices 110N, the care team device 130, the patient device 150, the foster parent device 160, the pharmacist device 170, the government device 180, and/or the health interface system 140 may include some or all of the components and/or functionality of the computer system 1500.

Computer system 1500 includes a bus 1502 or other communication mechanism for communicating information, and a hardware processor, or multiple processors, 1504 coupled with bus 1502 for processing information. Hardware processor(s) 1504 may be, for example, one or more general purpose microprocessors.

Computer system 1500 also includes a main memory 1506, such as a random access memory (RAM), cache and/or other dynamic storage devices, coupled to bus 1502 for storing information and instructions to be executed by processor 1504. Main memory 1506 also may be used for storing temporary variables or other intermediate information during execution of instructions to be executed by processor 1504. Such instructions, when stored in storage media accessible to processor 1504, render computer system 1500 into a special-purpose machine that is customized to perform the operations specified in the instructions.

Computer system 1500 further includes a read only memory (ROM) 1508 or other static storage device coupled to bus 1502 for storing static information and instructions for processor 1504. A storage device 1510, such as a magnetic disk, optical disk, or USB thumb drive (Flash drive), etc., is provided and coupled to bus 1502 for storing information and instructions.

Computer system 1500 may be coupled via bus 1502 to a display 1512, such as a cathode ray tube (CRT) or LCD display (or touch screen), for displaying information to a computer user. An input device 1514, including alphanumeric and other keys, is coupled to bus 1502 for communicating information and command selections to processor 1504. Another type of user input device is cursor control 1516, such as a mouse, a trackball, or cursor direction keys for communicating direction information and command selections to processor 804 and for controlling cursor movement on display 1512. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 1500 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage Computer system 1500 may implement the techniques described herein using customized hard-wired logic, one or more ASICs or FPGAs, firmware and/or program logic which in combination with the computer system causes or programs computer system 1500 to be a special-purpose machine. According to one embodiment, the techniques herein are performed by computer system 1500 in response to processor(s) 1504 executing one or more sequences of one or more instructions contained in main memory 1506. Such instructions may be read into main memory 1506 from another storage medium, such as storage device 1510. Execution of the sequences of instructions contained in main memory 1506 causes processor(s) 1504 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1510. Volatile media includes dynamic memory, such as main memory 1506. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a telephone line using a modem. A modem local to computer system 1500 can receive the data on the telephone line and use an infra-red transmitter to convert the data to an infra-red signal. An infra-red detector can receive the data carried in the infra-red signal and appropriate circuitry can place the data on bus 1502. Bus 1502 carries the data to main memory 1506, from which processor 1504 retrieves and executes the instructions. The instructions received by main memory 1506 may retrieve and execute the instructions. The instructions received by main memory 1506 may optionally be stored on storage device 1510 either before or after execution by processor 1504.

Computer system 1500 also includes a communication interface 1518 coupled to bus 1502. Communication interface 1518 provides a two-way data communication coupling to a network link 1520 that is connected to a local network 1522. For example, communication interface 1518 may be an integrated services digital network (ISDN) card, cable modem, satellite modem, or a modem to provide a data communication connection to a corresponding type of telephone line. As another example, communication interface 1518 may be a local area network (LAN) card to provide a data communication connection to a compatible LAN (or WAN component to communicated with a WAN). Wireless links may also be implemented. In any such implementation, communication interface 1518 sends and receives electrical, electromagnetic or optical signals that carry digital data streams representing various types of information.

Network link 1520 typically provides data communication through one or more networks to other data devices. For example, network link 1520 may provide a connection through local network 1522 to a host computer 1524 or to data equipment operated by an Internet Service Provider (ISP) 1526. ISP 1526 in turn provides data communication services through the world wide packet data communication network now commonly referred to as the "Internet" 1528. Local network 1522 and Internet 1528 both use electrical, electromagnetic or optical signals that carry digital data streams. The signals through the various networks and the signals on network link 1520 and through communication interface 1518, which carry the digital data to and from computer system 1500, are example forms of transmission media.

Computer system 1500 can send messages and receive data, including program code, through the network(s), network link 1520 and communication interface 1518. In the Internet example, a server 1530 might transmit a requested code for an application program through Internet 1528, ISP 1526, local network 1522 and communication interface 1518.

The received code may be executed by processor 1504 as it is received, and/or stored in storage device 1510, or other non-volatile storage for later execution.

Terminology

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computing system configured to access one or more databases in substantially real-time in order to aggregate patient health information and provide aggregated information to a user in an interactive user interface, the computing system comprising:
   one or more computer processors;
   a second database that organizes data in a plurality of first columns;
   a computer readable storage medium storing program instructions configured for execution by the one or more computer processor in order to cause the computing system to:
      for a first database in the one or more databases,
         access a dataset stored in the first database, wherein the accessed dataset comprises data for a plurality of users organized in a plurality of second columns;
         identify a name for a second column in the plurality of second columns in the accessed dataset;
         determine a mapping between the identified second column name and a name of a first column in the plurality of first columns, wherein the name of the first column is different than the identified second column name;
         store an unmodified version of data in the accessed dataset corresponding to the identified second column name in the second database in association with the name of the first column instead of the identified second column name; and
         cause display of the unmodified version of the data in the accessed dataset corresponding to the identified second column name in the interactive user interface under the name of the first column;

receive a request to access the computing system;

determine an identity of a user associated with the request to access the computing system;

retrieve, from the second database, user health data that is associated with the determined user;

retrieve, from a third database in the one or more databases, health claims data associated with the determined user;

generate a summary of a medical history of the determined user based on at least one of the retrieved user health data or the health claims data;

categorize the determined user into a first group based on the health claims data;

train one or more models using the health claims data and health claims data associated with one or more other users to produce a set of feature weights associated with the determined user, wherein each of the one or more models corresponds to a state transition from the first group to another group in one or more groups;

determine a likelihood that the determined user will transition from the first group into one of the one or more other groups within a threshold time period using the set of feature weights;

translate the likelihood into a risk score;

generate an alert associated with the user based on the retrieved user health data;

transmit the alert to a computing device separate from the computing system and operated by the user such that receipt of the alert by the computing device causes a browser to be automatically opened on the computing device and be redirected to a page for viewing the alert; and generate user interface data for rendering the interactive user interface on the computing device, wherein the interactive user interface includes a patient profile, wherein the patient profile comprises a medical profile section and a medical snapshot section, wherein the medical profile section comprises an indication of the risk score, wherein the medical snapshot section comprises a map indicating a location of a care team member associated with the determined user, wherein the interactive user interface, in response to selection of the care team member, further includes an input that, when selected, initiates, with the computing device, a contact to be established with the care team member via mobile communications.

2. The computing system of claim 1, wherein the interactive user interface includes a first container that comprises an identification of at least one third column in the plurality of first columns, wherein the first container further comprises the retrieved user health data that corresponds with the at least one third column and the generated summary of the medical history of the determined user.

3. The computing system of claim 1, wherein the retrieved health claims data comprises medical claims submitted on behalf of the determined user, and wherein the computer readable storage medium further stores program instructions that cause the computing system to generate the summary of the medical history of the determined user based on the medical claims.

4. The computing system of claim 1, wherein the computer readable storage medium further stores program instructions that cause the computing system to:

receive an indication that the generated alert is selected via the interactive user interface, wherein the generated alert indicates that the user missed an appointment; and update the user interface data such that the interactive user interface includes a first container comprising a list of selectable appointment times that can be reserved for the user.

5. The computing system of claim 1, wherein the computer readable storage medium further stores program instructions that cause the computing system to:

receive an indication that the generated alert is selected via the interactive user interface, wherein the generated alert indicates that the user is missing a lab test; and update the user interface data such that the interactive user interface includes a first container comprising a second map that graphically displays a location of one or more lab facilities located near the user where the lab test can be performed.

6. The computing system of claim 1, wherein the retrieved user health data comprises prescription data, and wherein the alert is generated based on the prescription data.

7. The computing system of claim 1, wherein the risk score is based on at least one of a number of missing services associated with the user, a priority of each missing service associated with the user, a likelihood that the user seeks medical services without intervention, or a number of times the user does not comply with a recommended care plan.

8. The computing system of claim 1, wherein the mapping between the identified second column name and the name of the first column is determined based on an ontology.

9. The computing system of claim 1, wherein the interactive user interface further includes a first container that comprises a first alert associated with a team member and a second alert associated with the team member, wherein the first alert corresponds with the user, and wherein the second alert corresponds with a second user.

10. The computing system of claim 1, wherein the computer readable storage medium further stores program instructions that cause the computing system to:

receive text and a selection of a second team member from a first team member; and transmit a message to an account associated with the second team member, wherein the message comprises the text, and wherein the second team member can view the message when accessing the computing system.

11. The computing system of claim 1, wherein the first team member is one of a primary care physician, a pharmacist, a government agency employee, a guardian, or the user.

12. A computer-implemented method of accessing one or more databases in substantially real-time in order to aggregate patient health information and provide the aggregated information to a user in an interactive user interface, the computer-implemented method comprising:

as implemented by one or more computer systems comprising computer hardware and memory, the one or more computer systems configured with specific executable instructions, retrieving a dataset stored in a first database, wherein the retrieved dataset comprises data for a plurality of users organized in a plurality of second columns;

identifying a name for a second column in the plurality of second columns in the retrieved dataset;

determining a mapping between the identified second column name and a name of a first column in a plurality of first columns, wherein the name of the first column is different than the identified second column name;

storing an unmodified version of data in the retrieved dataset corresponding to the identified second column name in a second database in association with the name of the first column instead of the identified second column name;

causing display of the unmodified version of the data in the retrieved dataset corresponding to the identified second column name in the interactive user interface under the name of the first column;

receiving a request to access the one or more computer systems;

determining an identity of a user associated with the request to access the one or more computer systems;

retrieving, from the second database, user health data that is associated with the determined user;

retrieving, from a third database in the one or more databases, health claims data associated with the determined user;

generating an alert associated with the user based on at least on of the retrieved user health data or the health claims data;

categorizing the determined user into a first group based on the health claims data;

training one or more models using the health claims data and health claims data associated with one or more other users to produce a set of feature weights associated with the determined user, wherein each of the one or more models corresponds to a state transition from the first group to another group in one or more groups;

determining a likelihood that the determined user will transition from the first group into one of the one or more other groups within a threshold time period using the set of feature weights;

translating the likelihood into a risk score;

transmitting the alert to a computing device separate from the one or more computing systems and operated by the user such that receipt of the alert by the computing device causes a browser to be automatically opened on the computing device and be redirected to a page for viewing the alert; and generating user interface data for rendering the interactive user interface on the computing device, wherein the interactive user interface includes a patient profile, wherein the patient profile comprises a medical profile section and a medical snapshot section, wherein the medical profile section comprises an indication of the risk score, wherein the medical snapshot section comprises a map indicating a location of a care team member associated with the determined user, wherein the interactive user interface, in response to selection of the care team member, further includes an input that, when selected, initiates, with the computing device, a contact to be established with the care team member via mobile communications.

13. The computer-implemented method of claim 12, wherein the interactive user interface includes a first container that comprises an identification of at least one third column in the plurality of first columns, wherein the first container further comprises the retrieved user health data that corresponds with the at least one third column.

14. The computer-implemented method of claim 13, further comprising generating a summary of a medical history of the determined user based on the retrieved user health data, wherein the first container further comprises the generated summary of the medical history of the determined user.

15. The computer-implemented method of claim 14, wherein the retrieved health claims data comprises medical claims submitted on behalf of the determined user, and wherein the computer-implemented method further comprises generating the summary of the medical history of the determined user based on the medical claims.

16. The computer-implemented method of claim 12, further comprising:
receiving an indication that the generated alert is selected via the interactive user interface, wherein the generated alert indicates that the user missed an appointment; and
updating the user interface data such that the interactive user interface includes a first container comprising a list of selectable appointment times that can be reserved for the user.

17. The computer-implemented method of claim 12, further comprising:
receiving an indication that the generated alert is selected via the interactive user interface, wherein the generated alert indicates that the user is missing a lab test; and
updating the user interface data such that the interactive user interface includes a first container comprising a second map that graphically displays a location of one or more lab facilities located near the user where the lab test can be performed.

18. The computer-implemented method of claim 12, wherein the retrieved health claims data comprises prescription data, and wherein the alert is generated based on the prescription data.

19. A non-transitory computer-readable storage medium including computer-executable instructions that, when executed by a processor, configure the processor to:
retrieve a dataset stored in a first database, wherein the retrieved dataset comprises data for a plurality of users organized in a plurality of second columns;
identify a name for a second column in the plurality of second columns in the retrieved dataset;
determine a mapping between the identified second column name and a name of a first column in a plurality of first columns, wherein the name of the first column is different than the identified second column name;
store an unmodified version of data in the retrieved dataset corresponding to the identified second column name in a second database in association with the name of the first column instead of the identified second column name;
cause display of the unmodified version of the data in the retrieved dataset corresponding to the identified second column name in an interactive user interface under the name of the first column;
receive a request to access one or more computer systems;
determine an identity of a user associated with the request to access the one or more computer systems;
retrieve, from the second database, user health data that is associated with the determined user;
retrieve, from a third database in the one or more databases, health claims data associated with the determined user;
categorize the determined user into a first group based on the health claims data;
train one or more models using the health claims data and health claims data associated with one or more other users to produce a set of feature weights associated with the determined user, wherein each of the one or more models corresponds to a state transition from the first group to another group in one or more groups;

determine a likelihood that the determined user will transition from the first group into one of the one or more other groups within a threshold time period using the set of feature weights;

translate the likelihood into a risk score;

generate an alert associated with the user based on the retrieved user health data;

transmit the alert to a computing device operated by the user such that receipt of the alert by the computing device causes a browser to be automatically opened on the computing device and be redirected to a page for viewing the alert; and generate user interface data for rendering the interactive user interface on the computing device, wherein the interactive user interface includes a patient profile, wherein the patient profile comprises a medical profile section and a medical snapshot section, wherein the medical profile section comprises an indication of the risk score, wherein the medical snapshot section comprises a map indicating a location of a care team member associated with the determined user, wherein the interactive user interface, in response to selection of the care team member, further includes an input that, when selected, initiates, with the computing device, a contact to be established with the care team member via mobile communications.

20. The computing system of claim 1, wherein the alert comprises a notification that a patient has a missing lab result, and wherein, in response to the notification, the interactive user interface includes a second map indicating a location of a health care provider closest to a location of the user and provides an input that, when selected, causes the browser to be redirected to a page that allows the user to schedule an appointment with the health care provider.

* * * * *